(12) United States Patent
Seiders et al.

(10) Patent No.: US 9,987,381 B2
(45) Date of Patent: Jun. 5, 2018

(54) RADIOLIGANDS FOR IMAGING THE LPA-1 RECEPTOR

(71) Applicants: BRISTOL-MYERS SQUIBB COMPANY, Princeton, NJ (US); YALE UNIVERSITY, New Haven, CT (US)

(72) Inventors: Thomas Jon Seiders, San Diego, CA (US); David J. Donnelly, Stockton, NJ (US); Samuel J. Bonacorsi, Jr., Flemington, NJ (US); Kai Cao, Princeton Junction, NJ (US); Tritin Tran, King of Prussia, PA (US); Adrienne Pena, South Plainfield, NJ (US); Joonyoung Kim, West Windsor, NJ (US); Richard E. Carson, Guilford, CT (US); Nabeel Nabulsi, Milford, CT (US); Jean-Dominique Gallezot, New Haven, CT (US); Yiyun Huang, Madison, CT (US); Jeffrey Roger Roppe, Temecula, CA (US)

(73) Assignees: BRISTOL-MYERS SQUIBB COMPANY, Princeton, NJ (US); YALE UNIVERSITY, New Haven, CT (US)

( * ) Notice: Subject to any disclaimer, the term of this patent is extended or adjusted under 35 U.S.C. 154(b) by 136 days.

(21) Appl. No.: 15/032,486

(22) PCT Filed: Oct. 31, 2014

(86) PCT No.: PCT/US2014/063391
§ 371 (c)(1),
(2) Date: Apr. 27, 2016

(87) PCT Pub. No.: WO2015/066456
PCT Pub. Date: May 7, 2015

(65) Prior Publication Data
US 2016/0256577 A1 Sep. 8, 2016

Related U.S. Application Data

(60) Provisional application No. 61/898,130, filed on Oct. 31, 2013.

(51) Int. Cl.
A61K 51/04 (2006.01)
C07D 261/14 (2006.01)
C07B 59/00 (2006.01)
A61B 6/00 (2006.01)

(52) U.S. Cl.
CPC .......... *A61K 51/0453* (2013.01); *A61B 6/481* (2013.01); *C07B 59/002* (2013.01); *C07D 261/14* (2013.01); *C07B 2200/05* (2013.01)

(58) Field of Classification Search
CPC .............................. A61K 31/00; C07D 261/14
See application file for complete search history.

(56) References Cited

U.S. PATENT DOCUMENTS 8,058,300 B2 * 11/2011 Hutchinson .......... C07D 261/14
514/380
2013/0253023 A1 9/2013 Brittain et al.

OTHER PUBLICATIONS

Ambrosini et al., "68 Ga-DOTANOC PET/CT Allows Somatostatin Receptor Imagining in Idiopathic Pulmonary Fibrosis: Preliminary Results," The Journal of Nuclear Medicine, vol. 51, No. 12, Dec. 2010, pp. 1950-1955.
Swaney et al., "A novel, orally active LPA1 receptor antagonist inhibits lung fibrosis in the mouse bleomycin model," British Journal of Pharmacology (2010), 160, pp. 1699-1713.
Groves et al., "Idiopathic Pulmonary Fibrosis and Diffuse Parenchymal Lung Disease: Implications from Initial Experience with 18 F-FDG PET/CT," The Journal of Nuclear Medicine, vol. 50, No. 4, Apr. 2009 pp. 538-545.
Lavalaye et al., "Imaging of Febrogenesis in Patients with Idiopathic Pulmonary Fibrosis with cis-4-[18 F]-Fluoro-L-Proline PET," Molecular Imaging and Biology (2009), 11:123-127.

* cited by examiner

*Primary Examiner* — Michael G Hartley
*Assistant Examiner* — Jagadishwar R Samala
(74) *Attorney, Agent, or Firm* — Hoffmann & Baron, LLP

(57) ABSTRACT

The present invention relates to radiolabeled LPA1 receptor antagonists or pharmaceutically acceptable salts thereof which are useful for the quantitative imaging of LPA1 receptors in mammals.

4 Claims, 2 Drawing Sheets

M1 = mouse #1  M2 = mouse #2  M3 = mouse #3

RADIOLIGANDS FOR IMAGING THE LPA-1 RECEPTOR

CROSS REFERENCE TO RELATED APPLICATIONS

This application is entitled to priority pursuant to 35 U.S.C. § 119(e) to U.S. provisional patent application No. 61/898,130, filed on Oct. 31, 2013, which is incorporated herein in its entirety.

FIELD OF THE INVENTION

The invention relates to novel radiolabeled lysophosphatidic acid (LPA) receptor 1 antagonists and their use in labeling and diagnostic imaging of LPA1 receptors in mammals.

BACKGROUND OF THE INVENTION

Positron emission tomography (PET) is a non-invasive imaging technique that can provide functional information about biological processes in living subjects. The ability to image and monitor in vivo molecular events, are great value to gain insight into biochemical and physiological processes in living organisms. This in turn is essential for the development of novel approaches for the treatment of diseases, early detection of disease and for the design of new drugs. PET relies on the design and synthesis of molecules labeled with positron-emitting radioisotope. These molecules are known as radiotracers or radioligands. For PET imaging, the most commonly used positron emitting (PET) radionuclides are; $^{11}C$, $^{18}F$, $^{15}O$ and $^{13}N$, all of which are cyclotron produced, and have half lives of 20, 110, 2 and 10 minutes, respectively. After being radiolabeled with a positron emitting radionuclide, these PET radioligands are administered to mammals, typically by intravenous (i.v.) injection. Once inside the body, as the radioligand decays it emits a positron that travels a small distance until it combines with an electron. An event known as an annihilation event then occurs, which generates two collinear photons with an energy of 511 keV each. Using a PET imaging scanner which is capable of detecting the gamma radiation emitted from the radioligand, planar and tomographic images reveal distribution of the radiotracer as a function of time. PET radioligands provide useful in-vivo information around target engagement and dose dependent receptor occupancy for human receptors.

Idiopathic pulmonary fibrosis (IPF) is a chronic disease that is characterized by the presence of scar tissue within the lungs, breathlessness, and chronic dry cough. IPF belongs to a family of lung disorders known as interstitial lung disease (ILD) and is associated with the pathological pattern known as usual interstitial pulmonary fibrosis (UIP). There are several potential clinical courses for IPF including slowly progressive disease (most common), disease marked by episodic acute exacerbations, or rapidly progressive disease. The median survival time from the time of diagnosis is between 2 and 5 years. To date, no therapies have been shown to impact the progression of IPF. The pathogenesis of IPF is unknown but one of the hypotheses is that an initial injury to epithelial cells increases lysophosphatidic acid (LPA) production. LPA is a bioactive phospholipid that regulates numerous aspects of cellular function and has been recognized as a novel mediator of wound healing and tissue fibrosis. LPA mediates its biological effects through the LPA receptors, of which at least six isoforms have been identified. Recent studies have recently linked the LPA1 isoform to the pathogenesis of lung fibrosis and the LPA1 receptor has been identified as a potential clinical target for IPF. Several findings support the role of LPA/LPA1 pathway in IPF which activates LPA1 receptors, leading to endothelial barrier breakdown, inflammation, and fibroblast recruitment/proliferation. LPA is elevated in bronchoalveolar lavage (BAL) of IPF patients. LPA concentrations are increased in BAL fluid (BALF) in persons with IPF and LPA1 antagonism inhibits fibroblast migration induced by IPF BALF. Also, knockout mice lacking the LPA1 receptor show reduced vascular leakage and decreased collagen accumulation in the lungs in a bleomycin model of fibrosis. Based on these data, LPA1 signaling is thought to contribute to the development of lung fibrosis, at least in part, through the induction of vascular leakage and stimulation of fibroblast migration.

Use of a specific PET radioligand having high affinity for the LPA1 receptor in conjunction with supporting imaging technology may provide a method for clinical evolution around both target engagement and dose/occupancy relationships of LPA1 antagonists in the human lung LPA1 or LPA1 in other organs such as the kidneys, liver, heart or skin. The invention described herein relates to radiolabeled LPA1 antagonists that would be useful for the exploratory and diagnostic imaging applications, both in-vitro and in-vivo, and for competition studies using radiolabeled and unlabeled LPA1 antagonists.

U.S. Pat. No. 8,058,300 discloses polycyclic antagonists of lysophosphatic acid receptors for use in treating LPA-dependent or LPA-mediated conditions or diseases such as fibrosis of various organs, including the lung.

SUMMARY

The present disclosure is based, in part, on the appreciation that radiolabeled lysophosphatidic acid (hereinafter "LPA1") receptor antagonists are useful in the detection and/or quantification and/or imaging of LPA1 receptors and/or LPA1 expression and/or affinity of a compound for occupying LPA1 receptors, in tissue of a mammalian species. It has been found that radiolabeled LPA1 receptor antagonists, when administered to a mammalian species, build up at or occupy LPA1 receptors and can be detected through imaging techniques, thereby providing valuable diagnostic markers for presence of LPA1 receptors, affinity of a compound for occupying LPA1 receptors, and clinical evaluation and dose selection of LPA1 receptor antagonists. In addition, the radiolabeled LPA1 receptor antagonists disclosed herein can be used as a research tool to study the interaction of unlabeled LPA1 receptor antagonists with LPA1 receptors in vivo via competition between the unlabeled drug and the radiolabeled drug for binding to the receptor. These types of studies are useful in determining the relationship between LPA1 receptor occupancy and dose of unlabeled LPA1 receptor antagonist, as well as for studying the duration of blockade of the receptor by various doses of unlabeled LPA1 receptor antagonists.

As a clinical tool, the radiolabeled LPA1 receptor antagonist can be used to help define clinically efficacious doses of LPA1 receptor antagonists. In animal experiments, the radiolabeled LPA1 receptor antagonist can be used to provide information that is useful for choosing between potential drug candidates for selection for clinical development.

The radiolabeled LPA1 receptor antagonist can also be used to study the regional distribution and concentration of LPA1 receptors in living lung tissue and other tissue, such as kidney, heart, liver and skin, of humans and animals and in tissue samples. They can be used to study disease or pharmacologically related changes in LPA1 receptor concentrations.

DETAILED DESCRIPTION OF THE INVENTION

Figure 1:
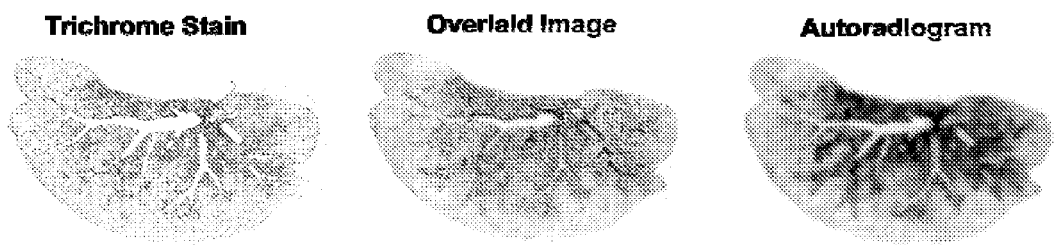
FIG. 1 shows a 10 μm thick lung tissue slice that has been imaged using autoradiography to determine LPA1 receptor binding.

In a first embodiment of the present disclosure are compounds which are radiolabeled LPA1 receptor antagonists or pharmaceutically acceptable salts thereof.

In yet another embodiment, the present disclosure provides a radiolabeled LPA1 receptor antagonist or a pharmaceutically acceptable salt thereof which is a positron emitting molecule with LPA1 receptor affinity.

In another embodiment, the present disclosure provides a radiolabeled LPA1 receptor antagonist where the radio label is an isotope of carbon or fluorine for use in positron emission tomography.

In yet another embodiment, the isotope is an isotope of $^{18}$F or $^{11}$C.

In still another embodiment, the LPA1 receptor antagonist is labeled with $^{18}$F, $^{11}$CH$_3$, —CH$_2$-$^{18}$F,

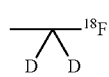

(where D is deuterium) or with $^{11}$C.

In other embodiments, the LPA1 receptor antagonist is:

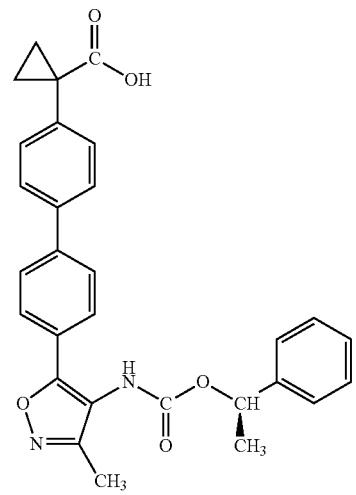

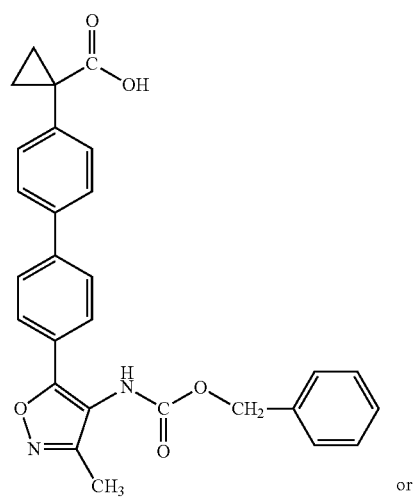

or

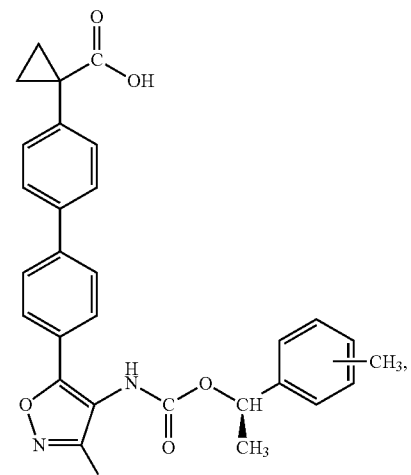

or a pharmaceutically acceptable salt thereof, and the LPA1 receptor antagonist is labeled with $^{11}$CH$_3$, $^{18}$F, —CH$_2$-$^{18}$F,

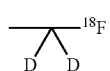
(where D is deuterium) or $^{11}C$.
In still another embodiment, the —$CH_2$-$^{18}F$ or
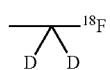
labeled LPA1 receptor antagonist has the following structure:
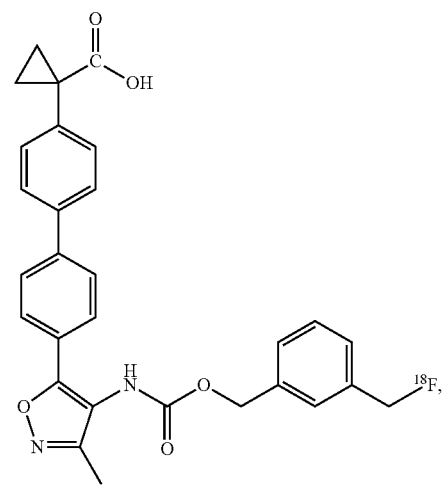
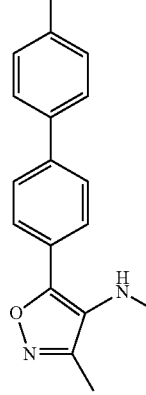
or a pharmaceutically acceptable salt thereof.
In still another embodiment, the radiolabeled receptor antagonist has the following structure:
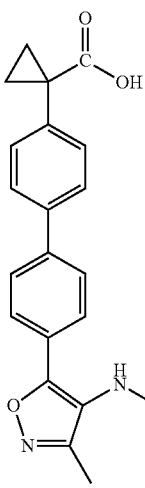
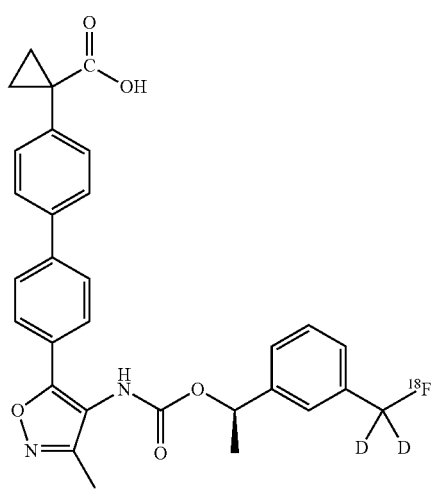
or
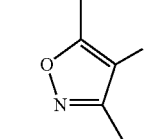
, -continued

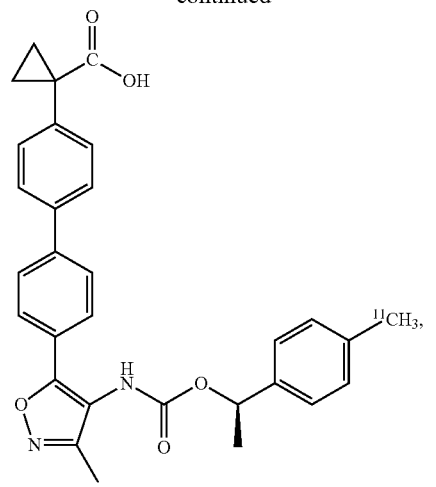

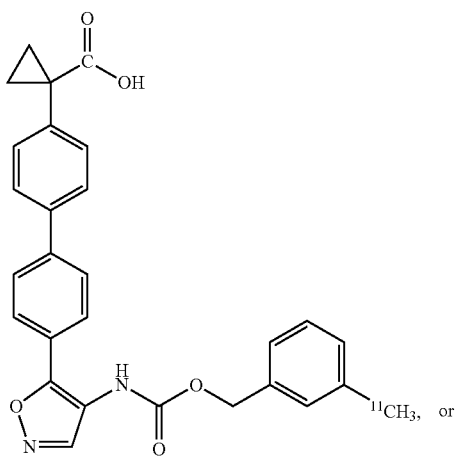

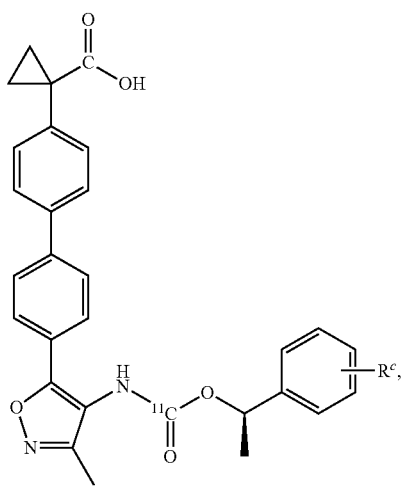

where $R^C$ is H or $CH_3$, or a pharmaceutically acceptable salt thereof.

In another embodiment, the $^{11}$C labeled LPA1 receptor antagonist has the following structure:

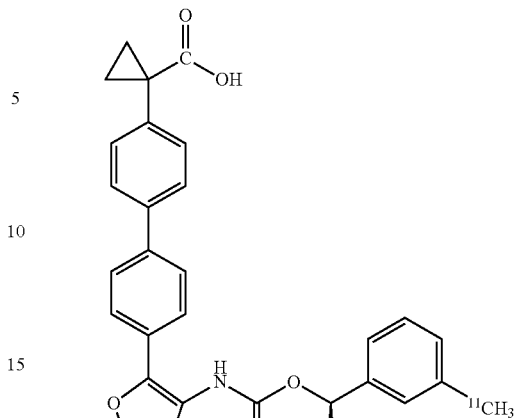

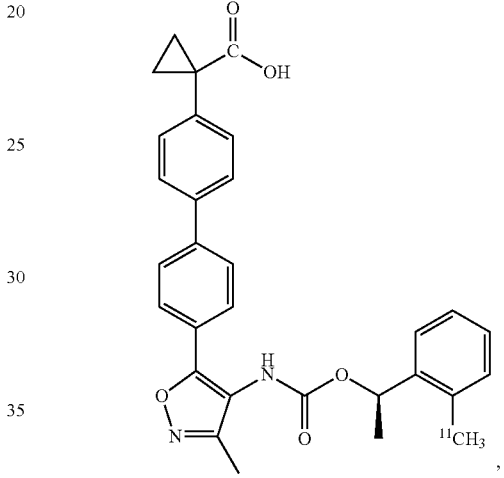

or a pharmaceutically acceptable salt thereof.

In another embodiment, the present disclosure provides a diagnostic composition for imaging LPA1 receptors which includes a radiolabeled LPA1 receptor antagonist and a pharmaceutically acceptable carrier therefor.

In still another embodiment, the present disclosure provides a radiopharmaceutical composition which includes a radiolabeled LPA1 receptor antagonist and a pharmaceutically acceptable carrier therefor.

In yet another embodiment, the present disclosure provides a method of autoradiography of mammalian tissues of known LPA1 expression, which includes the steps of administering a radiolabeled LPA1 receptor antagonist to a mammalian species, obtaining an image of the tissues by positron emission tomography, and detecting the radiolabeled compound in the tissues to determine LPA1 target engagement and LPA1 receptor occupancy of said tissues.

In still another embodiment, the present disclosure provides a method for the quantification or quantitative imaging of LPA1 receptors in mammalian tissue, which includes the steps of contacting such mammalian tissue in which such quantification or imaging is desired with an effective amount of a radiolabeled LPA1 receptor antagonist and detecting or quantifying the LPA receptors by detecting radioactive emission of the radioisotope, for example, by using positron emission tomography.

In another embodiment, the present disclosure provides a method of screening compound to determine its affinity for occupying LPA1 receptors in mammalian tissue, which includes the steps of administering to the mammal a radiolabeled compound to be tested or screened, obtaining an image of tissues bearing LPA1 receptors using positron emission tomography and detecting to what degree or extent such compound occupies LPA1 receptors.

In another embodiment, the present disclosure provides a method for the quantitative imaging of tissues bearing LPA1 receptors in a mammal, which includes the steps of contacting such mammalian tissue in which quantification is desired with a radiolabeled LPA1 receptor antagonist and detecting or quantifying the LPA1 receptors using positron emission tomography.

In yet another embodiment, the present disclosure provides a method for detecting an LPA1-dependent or LPA1-mediated fibrosis, which includes the method of imaging as disclosed above including the steps of contacting the desired mammalian tissue in which quantification is desired with an effective amount of a radiolabeled LPA1 receptor antagonist, detecting or quantifying the radioemission of the radioisotope from the LPA1 receptors, followed by the steps of comparing the radioactive emission from the radiolabeled LPA1 receptor antagonist for said patient with standard values, finding any significant deviation between said radioactive emission detected for said patient as compared with standard values, and attributing said deviation to the LPA1-dependent or LPA1-mediated fibrosis.

In another embodiment, the present disclosure provides a method for imaging one or more LPA1 receptors in a mammalian patient, which includes the steps of administering to the patient an imaging-effective amount of the radiolabeled LPA1 receptor antagonist, and then detecting the radioactive emission of said radiolabeled LPA1 receptor antagonist employing positron emission tomography.

In yet another embodiment, the radioactive emission is detected in the lungs, kidneys, liver or skin of said patient.

In another embodiment, the present disclosure provides a method for monitoring the treatment of a mammalian patient with a potentially useful LPA1 receptor antagonist to combat or treat LPA1-dependent or LPA1-mediated conditions or diseases, which includes the steps of administering to said patient in need of treatment the radiolabeled potentially useful LPA1 receptor antagonist, imaging tissues bearing LPA1 receptors in said patient, and detecting to what degree such radiolabeled potentially useful LPA1 receptor antagonist occupies LPA1 receptors using positron emission tomography.

In another embodiment, imaging of the tissues bearing LPA1 receptors is effected before, during and after treatment, with said radiolabeled LPA1 receptor antagonist.

In an embodiment of the methods of the present invention, the mammal or mammalian species is a human, dog, cat, ape, monkey, rat or mouse.

In another embodiment, the compounds of the invention may be prepared as Positron Emission Tomography (PET) tracers or radioligands for in vivo for imaging and quantification of LPA1 receptors.

Radiolabeled LPA1 receptor antagonists, when labeled with the appropriate radionuclide, are potentially useful for a variety of in vitro and/or in vivo imaging applications, including diagnostic imaging, basic research, and radiotherapeutic applications. Specific examples of possible diagnostic imaging and radiotherapeutic applications, include determining the location, the relative activity and/or quantifying of LPA1 receptors, radioimmunoassay of LPA1 receptor antagonists, and autoradiography to determine the distribution of LPA1 receptors in a mammal or an organ or tissue sample thereof.

In particular, the instant radiolabeled LPA1 receptor antagonists are useful for positron emission tomographic (PET) imaging of LPA1 receptors in the lung, heart, kidneys and other organs of living humans and experimental animals. These radiolabeled LPA1 receptor antagonists may be used as research tools to study the interaction of unlabeled LPA1 receptor antagonists with LPA1 receptors in vivo via competition between the unlabeled drug and the radiolabeled compound for binding to the receptor. These types of studies are useful for determining the relationship between LPA1 receptor occupancy and dose of unlabeled LPA1 receptor antagonist, as well as for studying the duration of blockade of the receptor by various doses of the unlabeled LPA1 receptor antagonist. As a clinical tool, the radiolabeled LPA1 receptor antagonists may be used to help define a clinically efficacious dose of an LPA1 receptor antagonist. In animal experiments, the radiolabeled LPA1 receptor antagonists can be used to provide information that is useful for choosing between potential drug candidates for selection for clinical development. The radiolabeled LPA1 receptor antagonists may also be used to study the regional distribution and concentration of LPA1 receptors in the human lung, kidney, heart, and other organs of living experimental animals and in tissue samples. The radiolabeled LPA1 receptor antagonists may also be used to study disease or pharmacologically related changes in LPA1 receptor concentrations.

For example, positron emission tomography (PET) tracers such as the present radiolabeled LPA1 receptor antagonists can be used with currently available PET technology to obtain the following information: relationship between level of receptor occupancy by candidate LPA1 receptor antagonists and clinical efficacy in patients; dose selection for clinical trials of LPA1 receptor antagonist prior to initiation of long term clinical studies; comparative potencies of structurally novel LPA1 receptor antagonists; investigating the influence of LPA1 receptor antagonists on in vivo transporter affinity and density during the treatment of clinical targets with LPA1 receptor antagonists; changes in the density and distribution of LPA1 receptors during effective and ineffective treatment of idiopathic pulmonary fibrosis, cardiac fibrosis, or other fibrotic diseases.

The present radiolabeled LPA1 receptor antagonists have utility in imaging LPA1 receptors or for diagnostic imaging with respect to a variety of disorders associated with LPA1 receptors.

The term "radiolabeled LPA1 receptor antagonist" refers to an LPA1 receptor antagonist labeled with a positron emitting radionuclide which is an isotope of a carbon or fluorine.

The terms "fibrosis" or "fibrosing disorder", as used herein, refers to conditions that are associated with the abnormal accumulation of cells and/or fibronectin and/or collagen and/or increased fibroblast recruitment and include but are not limited to fibrosis of individual organs or tissues such as the heart, kidney, liver, joints, lung, pleural tissue, peritoneal tissue, skin, cornea, retina, musculoskeletal and digestive tract, such as idiopathic pulmonary fibrosis, scleroderma, and chronic nephropathies.

Exemplary diseases, disorders, or conditions that involve fibrosis include, but are not limited to: lung diseases associated with fibrosis, e.g., idiopathic pulmonary fibrosis, pulmonary fibrosis secondary to systemic inflammatory disease such as rheumatoid arthritis, scleroderma, lupus, cryptogenic fibrosing alveolitis, radiation induced fibrosis, chronic obstructive pulmonary disease (COPD), chronic asthma, silicosis, asbestos induced pulmonary or pleural fibrosis, acute lung injury and acute respiratory distress (including bacterial pneumonia induced, trauma induced, viral pneumonia induced, ventilator induced, non-pulmonary sepsis induced, and aspiration induced); chronic nephropathies associated with injury/fibrosis (kidney fibrosis), e.g., glomerulonephritis secondary to systemic inflammatory diseases such as lupus and scleroderma, diabetes, glomerular nephritis, focal segmental glomerular sclerosis, IgA nephropathy, hypertension, allograft and Alport; gut fibrosis, e.g., scleroderma, and radiation induced gut fibrosis; liver fibrosis, e.g., cirrhosis, alcohol induced liver fibrosis, nonalcoholic steatohepatitis (NASH), biliary duct injury, primary biliary cirrhosis, infection or viral induced liver fibrosis (e.g., chronic HCV infection), and autoimmune hepatitis; head and neck fibrosis, e.g., radiation induced; corneal scarring, e.g., LASIK (laser-assisted in situ keratomileusis), corneal transplant, and trabeculectomy; hypertrophic scarring and keloids, e.g., burn induced or surgical; and other fibrotic diseases, e.g., sarcoidosis, scleroderma, spinal cord injury/fibrosis, myelofibrosis, vascular restenosis, atherosclerosis, arteriosclerosis, Wegener's granulomatosis, mixed connective tissue disease, and Peyronie's disease.

Other diseases, disorders, or conditions where LPA1 receptors may be involved include atherosclerosis, thrombosis, heart disease, vasculitis, formation of scar tissue, restenosis, phlebitis, COPD (chronic obstructive pulmonary disease), pulmonary hypertension, pulmonary fibrosis, pulmonary inflammation, bowel adhesions, bladder fibrosis and cystitis, fibrosis of the nasal passages, sinusitis, inflammation mediated by neutrophils, and fibrosis mediated by fibroblasts, dermatological disorders including proliferative or inflammatory disorders of the skin such as, atopic dermatitis, bullous disorders, collagenosis, psoriasis, psoriatic lesions, dermatitis, contact dermatitis, eczema, rosacea, wound healing, scarring, hypertrophic scarring, keloids, Kawasaki Disease, rosacea, Sjögren-Larsson Syndrome, and urticaria, respiratory diseases including asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia, and inflammatory/immune disorders including psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjögren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

For the use of the instant compounds as exploratory or diagnostic imaging agents, the radiolabeled compounds may be administered to mammals, preferably humans, in a pharmaceutical composition, either alone or, preferably, in combination with pharmaceutically acceptable carriers or diluents, optionally with known adjuvants, such as alum, in a pharmaceutical composition, according to standard pharmaceutical practice. Such compositions can be administered orally or parenterally, including the intravenous, intramuscular, intraperitoneal, subcutaneous, rectal and topical routes of administration. Preferably, administration is intravenous. The LPA1 receptor antagonists are radiotracers labeled with short-lived, positron emitting radionuclides and thus are generally administered via intravenous injection within less than one hour of their synthesis. This is necessary because of the short half-life of the radionuclides involved (20 and 110 minutes for C-11 and F-18, respectively).

An appropriate dosage level for the unlabeled LPA1 receptor antagonist is disclosed in U.S. Pat. No. 8,058,300, namely, 0.01 to 5000 mg per day or 1 to 1000 mg per day.

When the present radiolabeled LPA1 receptor antagonist is administered into a human subject, the amount required for imaging will normally be determined by the prescribing physician with the dosage generally varying according to the quantity of emission from the radionuclide. However, in most instances, an effective amount will be the amount of compound sufficient to produce emissions in the range of from about 1-5 mCi.

In one exemplary application, administration occurs in an amount of radiolabeled LPA1 receptor antagonist of between about 0.005 µg/kg of body weight to about 50 µg/kg of body weight per day, usually between 0.02 µg/kg of body weight to about 3 µg/kg of body weight. The mass associated with a PET tracer is in the form of the natural isotope, for example, $^{12}C$ for an $^{11}C$ PET tracer and $^{19}F$ for an $^{18}F$ PET tracer, respectively. A particular analytical dosage for the instant composition includes from about 0.5 µg to about 100 µg of a labeled LPA1 receptor antagonist. The dosage will usually be from about 1 µg to about 50 µg of a radiolabeled LPA1 receptor antagonist.

The following illustrative procedure may be utilized when performing PET imaging studies on patients in the clinic. The patient is premedicated with unlabeled LPA1 receptor antagonist some time prior to the day of the experiment and is fasted for at least 12 hours allowing water intake ad libitum. A 20 G two-inch venous catheter is inserted into the contralateral ulnar vein for radiotracer administration. Administration of the PET tracer is often timed to coincide with time of maximum ($T_{max}$) or minimum ($T_{min}$) of LPA1 receptor antagonist concentration in the blood.

The patient is positioned in the PET camera and a tracer dose of the PET tracer of radiolabeled LPA1 receptor antagonist such as [$^{11}C$] Example 1 (<20 mCi) is administered via i.v. catheter. Either arterial or venous blood samples are taken at appropriate time intervals throughout the PET scan in order to analyze and quantitate the fraction of unmetabolized PET tracer of [$^{11}C$] Example 1 in plasma. Images are acquired for up to 120 min. Within ten minutes of the injection of radiotracer and at the end of the imaging session, 1 ml blood samples are obtained for determining the plasma concentration of any unlabeled LPA1 receptor antagonist which may have been administered before the PET tracer.

Tomographic images are obtained through image reconstruction. For determining the distribution of radiotracer, regions of interest (ROIs) are drawn on the reconstructed image including, but not limited to, the lungs, liver, heart, kidney, skin or other organs and tissue. Radiotracer uptakes over time in these regions are used to generate time activity curves (TAC) obtained in the absence of any intervention or in the presence of the unlabeled LPA1 receptor antagonist at the various dosing paradigms examined. Data are expressed as radioactivity per unit time per unit volume (μCi/cc/mCi injected dose). TAC data are processed with various methods well-known in the field to yield quantitative parameters, such as Binding Potential (BP) or Volume of Distribution ($V_T$), that are proportional to the density of unoccupied LPA1 receptor Inhibition of LPA1 receptor is then calculated based on the change of BP or $V_T$ by equilibrium analysis in the presence of LPA1 receptor antagonists at the various dosing paradigms as compared to the BP or $V_T$ in the unmedicated state Inhibition curves are generated by plotting the above data vs the dose (concentration) of LPA1 receptor antagonists. Inhibition of LPA1 receptor is then calculated based on the maximal reduction of PET radioligand's $V_T$ or BP that can be achieved by a blocking drug at $E_{max}$, $T_{max}$ or $T_{min}$ and the change of its non-specific volume of distribution ($V_{ND}$) and the BP in the presence of LPA1 receptor antagonists at the various dosing paradigms as compared to the BP or $V_T$ in the unmedicated state. The ID50 values are obtained by curve fitting the dose-rate/inhibition curves.

The present invention is further directed to a method for the diagnostic imaging of LPA1 receptors in a mammal in need thereof which includes the step of combining radiolabeled LPA1 receptor antagonist with a pharmaceutical carrier or excipient.

Certain Terminology

Unless otherwise stated, the following terms used in this application, including the specification and claims, have the definitions given below. It must be noted that, as used in the specification and the appended claims, the singular forms "a", "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes", and "included", is not limiting. The section headings used herein are for organizational purposes only and are not to be construed as limiting the subject matter described.

An "alkyl" refers to an aliphatic hydrocarbon containing 1 to 8 carbons. The alkyl may be saturated or unsaturated. The alkyl, whether saturated or unsaturated, is a branched alkyl or straight chain alkyl. Typical alkyl groups include, but are in no way limited to, methyl, ethyl, propyl, isopropyl, butyl, isobutyl, sec-butyl, tertiary butyl, pentyl, neopentyl, hexyl, allyl, but-2-enyl, but-3-enyl, and the like.

An "alkoxy" group refers to a (alkyl)O— group, where alkyl is as defined herein.

"Cycloalkyl" refers to cyclopropyl, cyclopropenyl, cyclobutyl, cyclobutenyl, cyclopentyl, cyclopentenyl, cyclohexyl, or cyclohexenyl.

The term "halo" or, alternatively, "halogen" or "halide" means fluoro, chloro, bromo or iodo.

The term "fluoroalkyl" refers to an alkyl in which one or more hydrogen atoms are replaced by a fluorine atom.

The term "heteroalkyl" refers to an alkyl group in which one or more skeletal atoms of the alkyl are selected from an atom other than carbon, e.g., oxygen, nitrogen (e.g., NH or Nalkyl), sulfur, or combinations thereof. In some embodiments, one aspect, heteroalkyl refers to an alkyl group in which one of the skeletal atoms of the alkyl is oxygen.

The term "optionally substituted" or "substituted" means that the referenced group may be substituted with one or more additional group(s) individually and independently selected from halogen, —CN, —NH$_2$, —OH, —NH(CH$_3$), —N(CH$_3$)$_2$, alkyl, cycloalkyl, fluoroalkyl, heteroalkyl, alkoxy, fluoroalkoxy, —S-alkyl, or —S(=O)$_2$alkyl. In some embodiments, an optional substituent is selected from halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, substituted groups are substituted with one of the preceding groups.

The term "acceptable" with respect to a formulation, composition or ingredient, as used herein, means having no persistent detrimental effect on the general health of the subject being treated.

The term "modulate", as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator", as used herein, refers to a molecule that interacts with a target either directly or indirectly. The interactions include, but are not limited to, the interactions of an agonist, partial agonist, an inverse agonist and antagonist. In one embodiment, a modulator is an antagonist.

The term "agonist", as used herein, refers to a molecule such as a compound, a drug, an enzyme activator or a hormone modulator that binds to a specific receptor and triggers a response in the cell. An agonist mimics the action of an endogenous ligand (such as LPA, prostaglandin, hormone or neurotransmitter) that binds to the same receptor.

The term "antagonist", as used herein, refers to a molecule such as a compound, which diminishes, inhibits, or prevents the action of another molecule or the activity of a receptor site. Antagonists include, but are not limited to, competitive antagonists, non-competitive antagonists, uncompetitive antagonists, partial agonists and inverse agonists.

The term "LPA-dependent", as used herein, refers to conditions or disorders that would not occur, or would not occur to the same extent, in the absence of LPA.

The term "LPA-mediated", as used herein, refers to refers to conditions or disorders that might occur in the absence of LPA but can occur in the presence of LPA.

The terms "co-administration" or the like, as used herein, are meant to encompass administration of the selected therapeutic agents to a single patient, and are intended to include treatment regimens in which the agents are administered by the same or different route of administration or at the same or different time.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or ignore of the ingredient. Accordingly, the pharmaceutical compositions of the present invention encompass any composition made by mixing a compound of the present invention and a pharmaceutically acceptable carrier. By "pharmaceutically acceptable" it is meant the carrier, diluent or excipient must be compatible with the other ingredients of the formulation and not deleterious to the recipient thereof. The terms "administration of" and or "administering a" compound should be understood to mean providing a compound of the invention or a prodrug of a compound of the invention to the patient.

The terms "effective amount" or "therapeutically effective amount", as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The term "pharmaceutical combination" as used herein, means a product that results from the mixing or combining of more than one active ingredient and includes both fixed and non-fixed combinations of the active ingredients. The term "fixed combination" means that the active ingredients, e.g., a compound of Formula (I) and a co-agent, are both administered to a patient simultaneously in the form of a single entity or dosage. The term "non-fixed combination" means that the active ingredients, e.g., a compound of Formula (I) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g., the administration of three or more active ingredients.

The term "subject" or "patient" encompasses mammals. Examples of mammals include, but are not limited to, humans, chimpanzees, apes, monkey, cattle, horses, sheep, goats, swine, rabbits, dogs, cats, rodents, rats, mice guinea pigs, and the like. In one embodiment, the mammal is a human.

The terms "treat", "treating" or "treatment", as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The compounds herein described may have asymmetric centers. Such compounds containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis- and trans-geometric isomers of the compounds disclosed are described and may be isolated as a mixture of isomers or as separated isomeric forms. All chiral, diastereomeric, racemic forms, and all geometric isomeric forms of a structure are intended, unless the specific stereochemistry or isomeric form is specifically indicated.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof.

The terms pharmaceutically acceptable "salt" and "salts" may refer to basic salts formed with inorganic and organic bases. Such salts include ammonium salts; alkali metal salts, such as lithium, sodium, and potassium salts; alkaline earth metal salts, such as calcium and magnesium salts; salts with organic bases, such as amine like salts (e.g., dicyclohexylamine salt, benzathine, N-methyl-D-glucamine, and hydrabamine salts); and salts with amino acids like arginine, lysine, and the like; and zwitterions, the so-called "inner salts". Nontoxic, pharmaceutically acceptable salts are preferred, although other salts are also useful, e.g., in isolating or purifying the product.

The term pharmaceutically acceptable "salt" and "salts" also includes acid addition salts. These are formed, for example, with strong inorganic acids, such as mineral acids, for example sulfuric acid, phosphoric acid, or a hydrohalic acid such as HCl or HBr, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic, or terephthalic acid, such as hydroxycarboxylic acids, for example ascorbic, glycolic, lactic, malic, tartaric, or citric acid, such as amino acids, (for example aspartic or glutamic acid or lysine or arginine), or benzoic acid, or with organic sulfonic acids, such as ($C_1$-$C_4$) alkyl or arylsulfonic acids, which are unsubstituted or substituted, for example by halogen, for example methanesulfonic acid or p-toluenesulfonic acid.

The pharmaceutically acceptable salts can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th Edition, p. 1418, Mack Publishing Company, Easton, Pa. (1985), the disclosure of which is hereby incorporated by reference.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

SYNTHESIS OF COMPOUNDS

The synthesis of the compounds of the present invention is illustrated in the following Schemes, using the compounds as disclosed in the working Example as representative. The starting material 1 employed in the following Schemes is disclosed in U.S. Pat. No. 8,058,300, the disclosure of which in its entirety is incorporated herein by reference.

A procedure for the synthesis of the unlabeled compounds of Formula (I) is outlined below in Scheme 1 and illustrated in Example 1, Part A:

Scheme 1

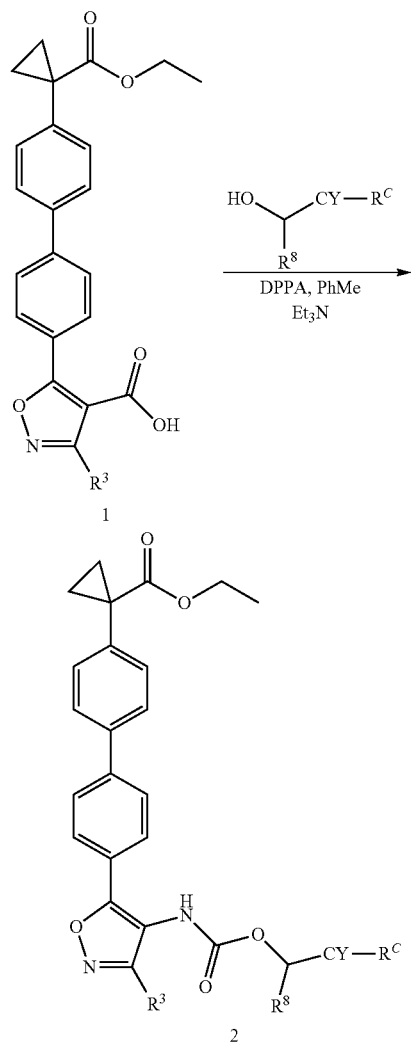

In Scheme 2, the synthesis of an [$^{11}$C] radiotracer compound from the precursor Intermediate 1 is shown, as a general illustration of the methodology used herein to prepare such radiolabeled LPA1 receptor antagonists.

Scheme 2

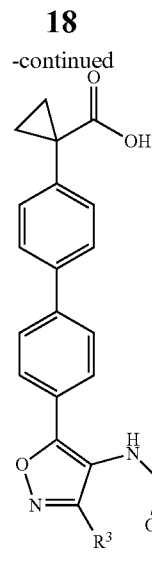

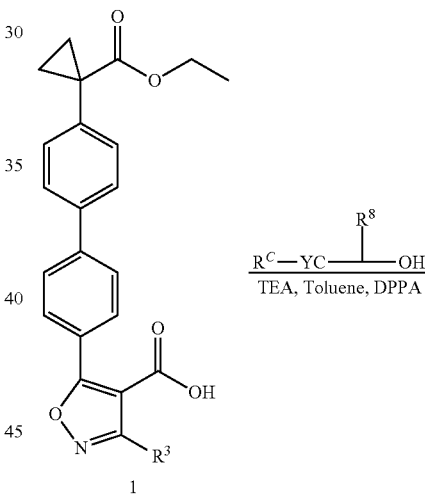

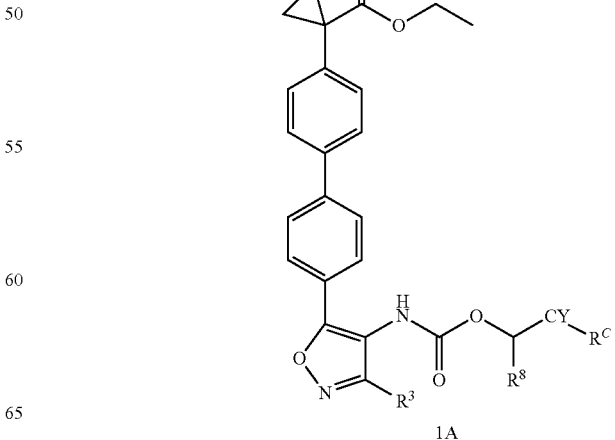

Scheme 3
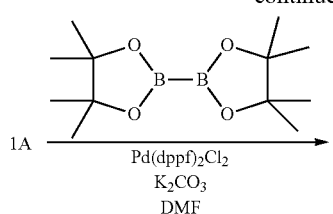
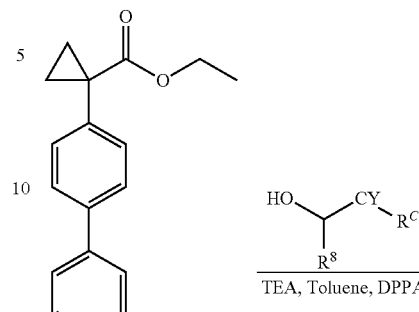
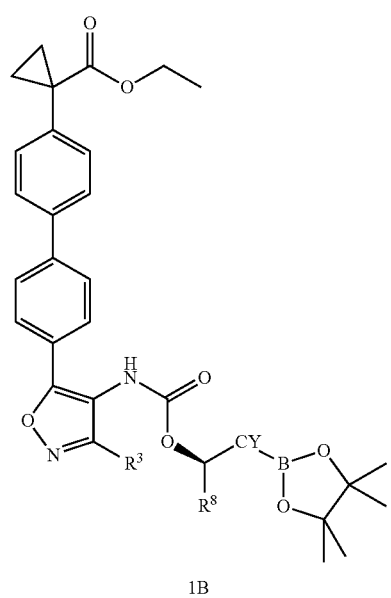
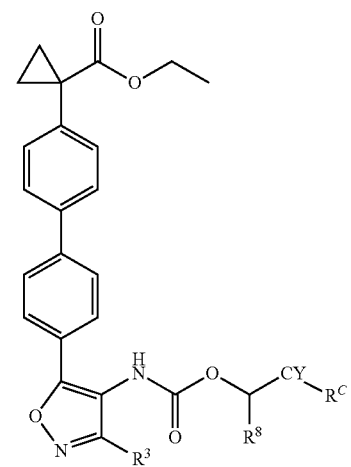
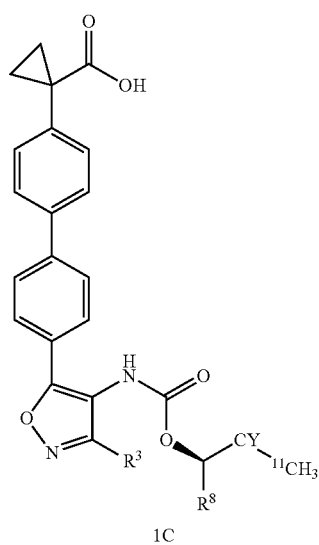
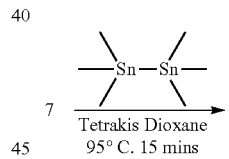
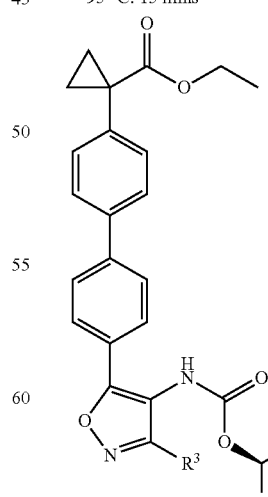
In Scheme 3, the synthesis of the [$^{11}$C] radiotracer compound from the precursor Intermediate 8 is shown, as a general illustration of the methodology used herein to prepare such radiolabeled LPA1 receptor antagonists.

-continued

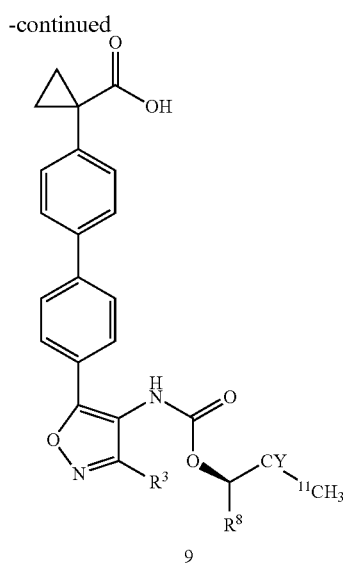

9

In Scheme 4, the synthesis of the [¹¹C] radiotracer compound from the precursor Intermediate 10 (prepared as described in Example 3, Part A) is shown, as a general illustration of the methodology used herein to prepare such radiolabeled LPA1 receptor antagonists.

In Scheme 5, the synthesis from the precursor Intermediate 12 is shown, as a general illustration of the methodology used herein to prepare such radiolabeled LPA1 receptor antagonists.

Scheme 5

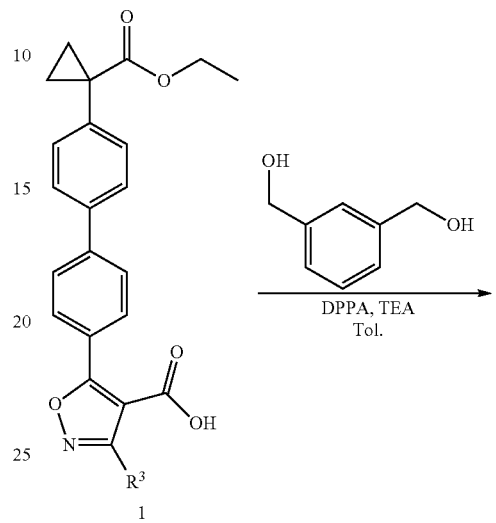

Scheme 4

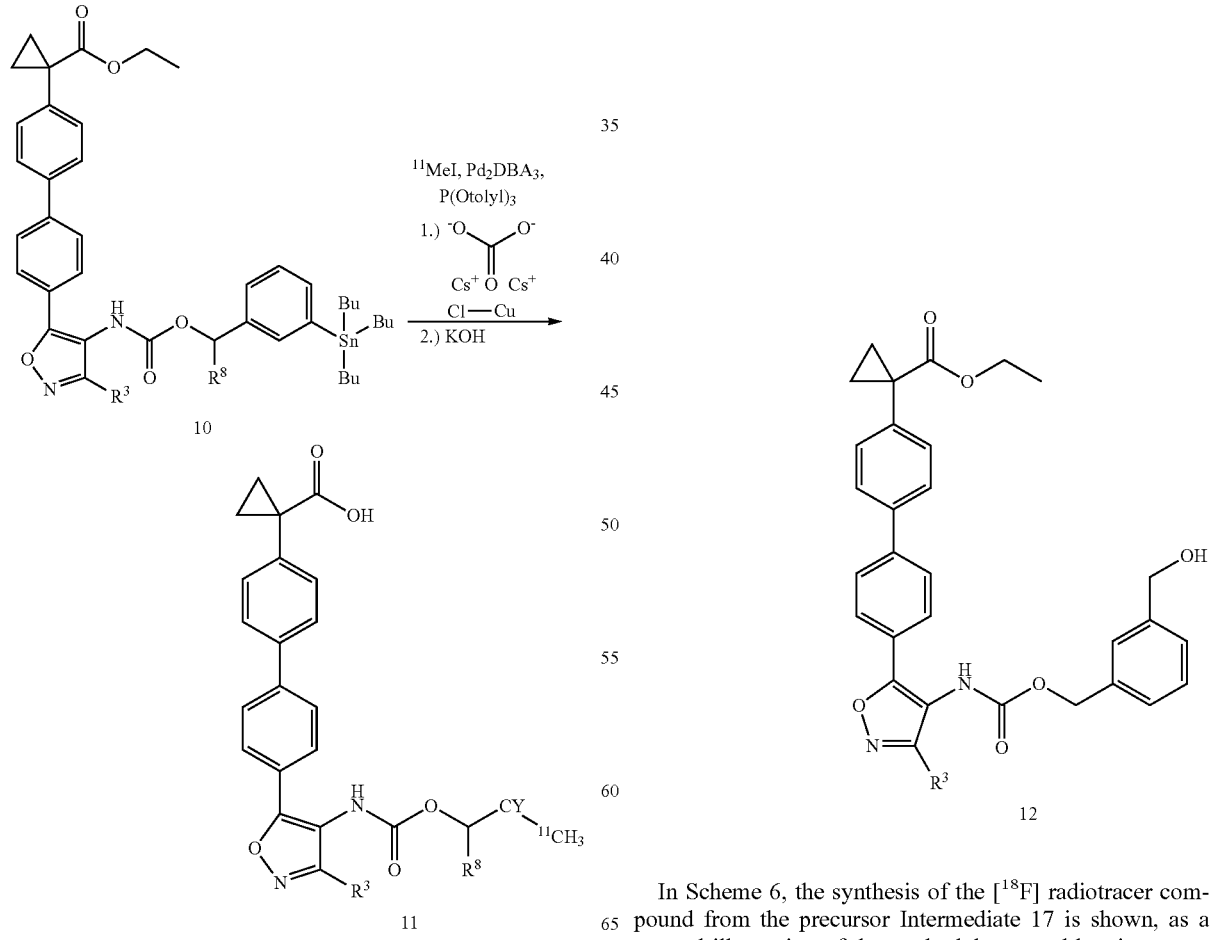

In Scheme 6, the synthesis of the [¹⁸F] radiotracer compound from the precursor Intermediate 17 is shown, as a general illustration of the methodology used herein to prepare such radiolabeled LPA1 receptor antagonists.

Scheme 6
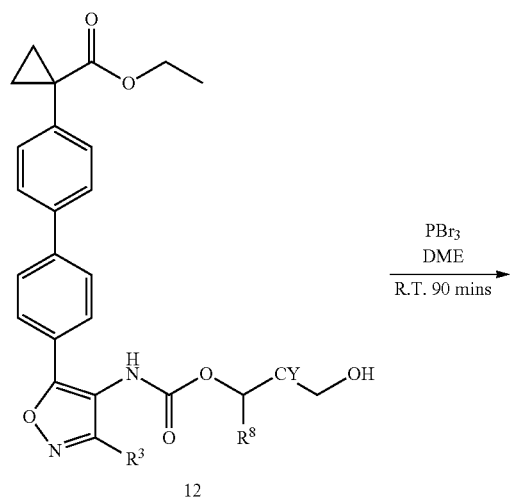
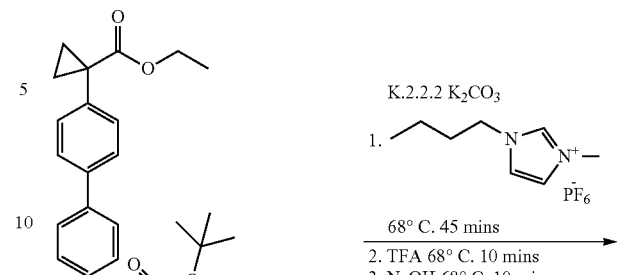
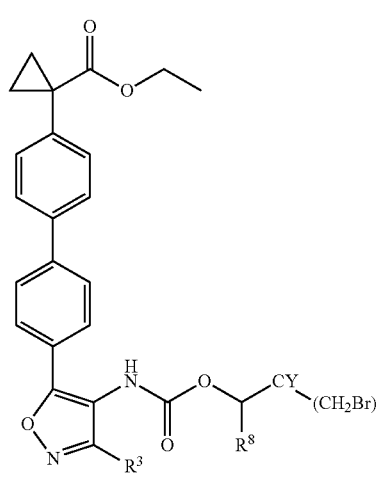
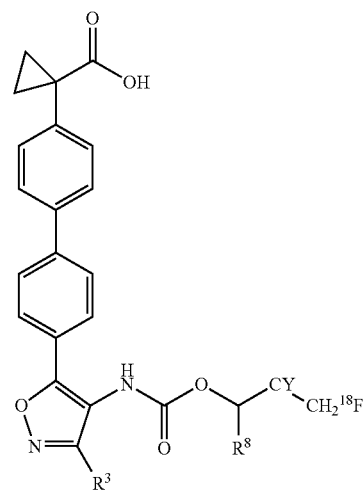
In Scheme 7, the synthesis of a
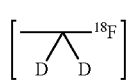
radiotracer is outlined below and illustrated in Example 7.

Scheme 7
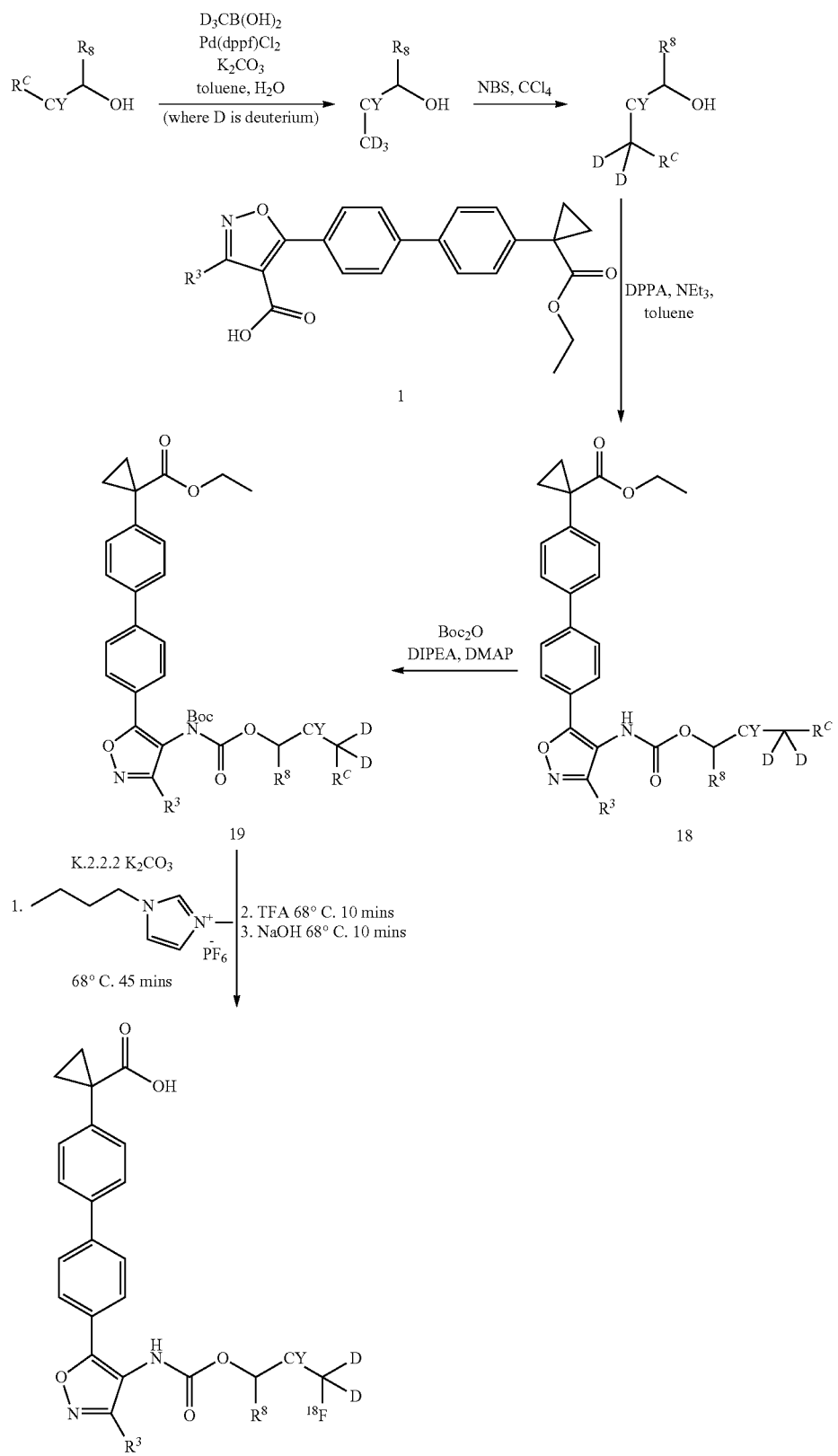

In Scheme 8, the synthesis of another [$^{11}$C] radiotracer compound is outlined below and illustrated in Example 8.
Scheme 8
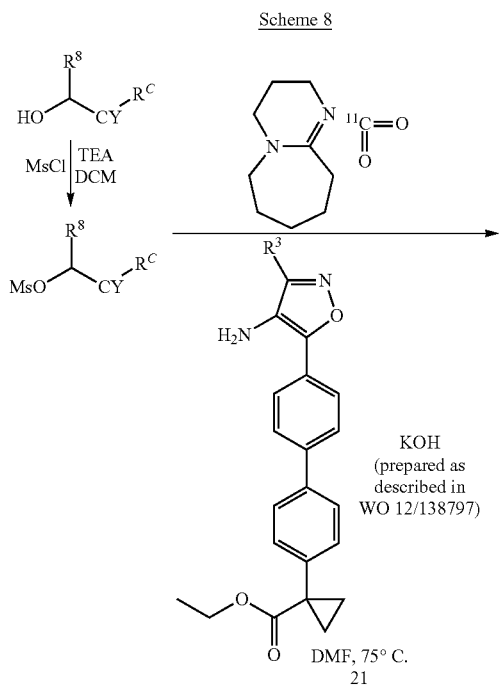
EXAMPLES
The following Examples are illustrative only and should not be construed as limiting the invention thereto.
Example 1
[11C]-(R)-1-(4'-(3-Methyl-4-(((1-(m-tolyl)ethoxy)carbonyl)amino)isoxazol-5-yl)-[1,1'-biphenyl]-4-yl)cyclopropanecarboxylic acid (BMT-136088)
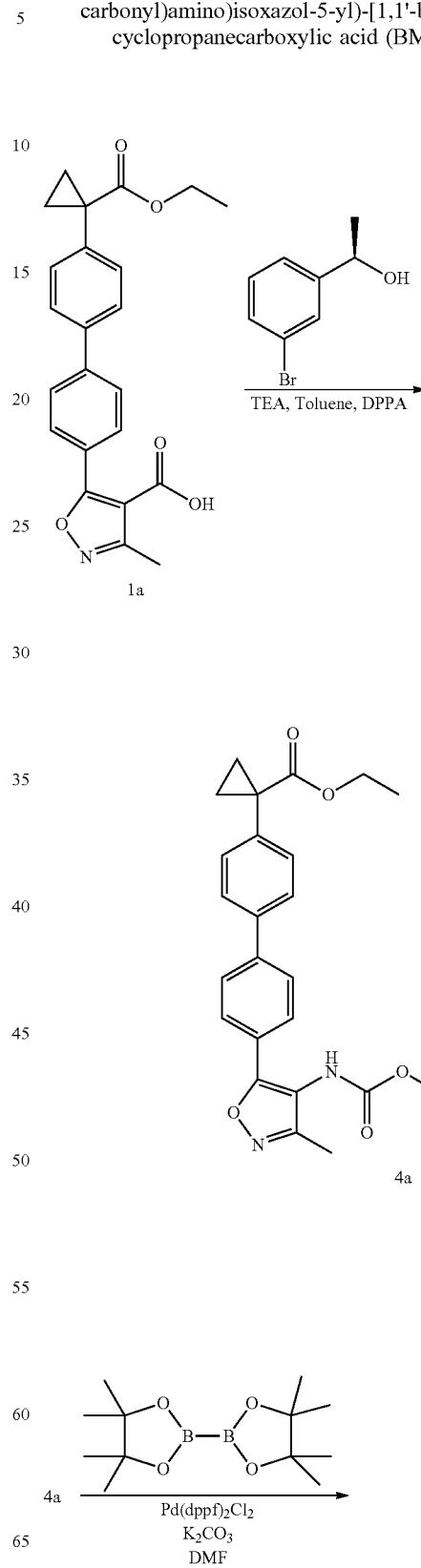

A. Synthesis of (R)-ethyl 1-(4'-(4-(((1-(3-bromophenyl)ethoxy)carbonyl)amino)-3-methylisoxazol-5-yl)-[1,1'-biphenyl]-4-yl)cyclopropanecarboxylate, Intermediate (4a)

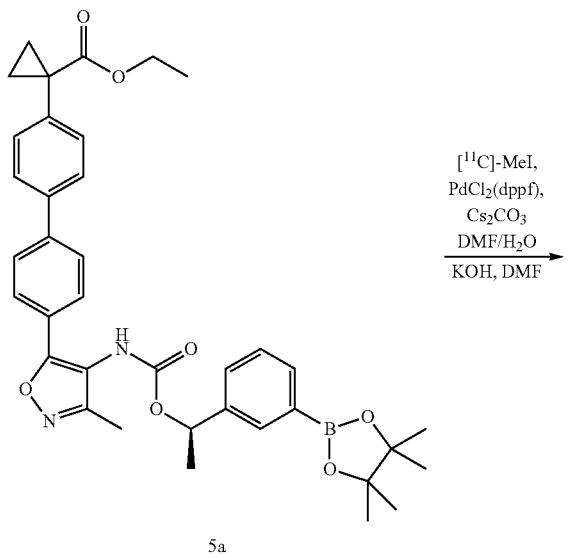

5a

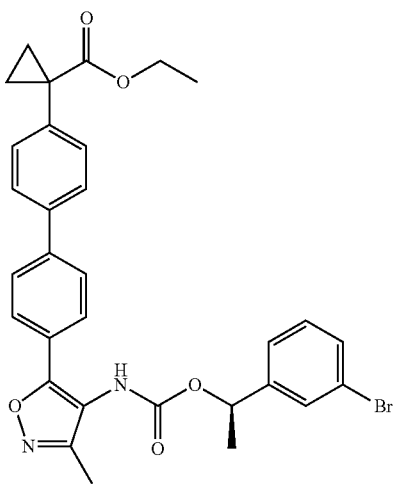

4a

Triethylamine (1.691 mL, 12.14 mmol) was added to a stirring solution of 5-(4'-(1-(ethoxycarbonyl)cyclopropyl)-[1,1'-biphenyl]-4-yl)-3-methylisoxazole-4-carboxylic acid (Intermediate 1a, prepared as described in U.S. Pat. No. 8,058,300) (2.0 g, 4.85 mmol) in toluene (60 mL) at ambient temperature. Diphenyl phosphoryl azide (1.151 mL, 5.34 mmol) was then added to the resulting reaction mixture and the entire contents were stirred at 80° C. for 15 minutes under a steady stream of nitrogen gas. To this reaction mixture, was added (R)-3-bromo-alpha-methylbenzyl alcohol (0.769 mL, 5.34 mmol, 98% e.e.) and the resultant reaction mixture was stirred at 80° C. under nitrogen gas for 17 hours. The crude reaction mixture was then concentrated in vacuo at 60° C. to give a light brown oil. The crude reaction mixture was loaded onto a 80 gram silica cartridge and was purified using an ISCO CombiFlash companion flash system. The UV was monitored at 254 nm and the flow rate of this purification was 60 mL/min. The normal phase solvents used were; Solvent A: hexane, Solvent B: ethyl acetate. Using the following gradient method: 0 min-0% B, 15 min-60% B, 20 min-60% B, 30 min-100% B, the purified product eluted between the 10-13 minute marks. Pooled product fractions were evaporated under reduced pressure to give the desired product (R)-ethyl 1-(4'-(4-(((1-(3-bromophenyl)ethoxy)carbonyl)amino)-3-methylisoxazol-5-yl)-[1,1'-biphenyl]-4-yl)cyclopropanecarboxylate as a colorless solid (Intermediate 4a) (2.70 g, 4.02 mmol, 83.0% yield). $^1$H NMR (400 MHz, chloroform-d) δ 7.80 (br. s., 2H), 7.66 (d, J=8.4 Hz, 2H), 7.63-7.51 (m, 3H), 7.51-7.41 (m, 3H), 6.12 (br. s., 1H), 5.84 (br. s., 1H), 4.14 (q, J=7.0 Hz, 2H), 2.26 (s, 3H), 1.70-1.63 (m, 3H), 1.61 (s, 3H), 1.26-1.17 (m, 5H). LCMS m/z (M+H) theory: 589.13, 591.13 found: 589.33, 591.25.

[$^{11}$C]-MeI, PdCl$_2$(dppf), Cs$_2$CO$_3$ DMF/H$_2$O
KOH, DMF

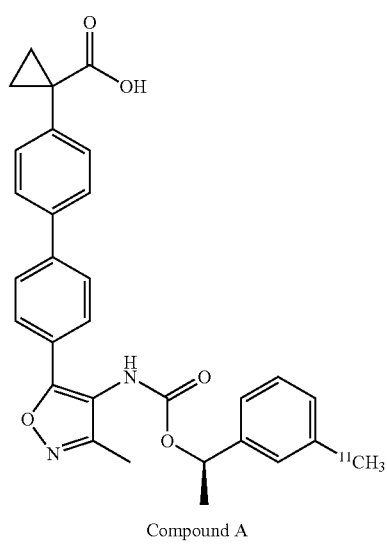

Compound A

B. Synthesis of (R)-ethyl 1-(4'-(3-methyl-4-(((1-(3-(4,4,5,5-tetramethyl-1,3,2-dioxaborolan-2-yl)phenyl)ethoxy)carbonyl)amino)isoxazol-5-yl)-[1,1'-biphenyl]-4-yl)cyclopropanecarboxylate, Intermediate (5a)

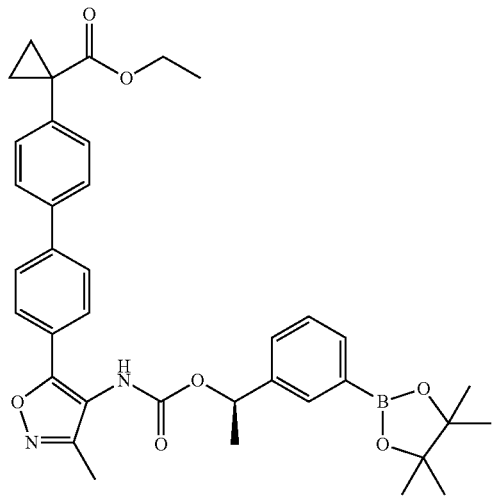

A mixture of Part A (R)-ethyl 1-(4'-(4-(((1-(3-bromophenyl)ethoxy)carbonyl)amino)-3-methylisoxazol-5-yl)-[1,1'-biphenyl]-4-yl)cyclopropanecarboxylate (700 mg, 1.187 mmol), 4,4,4',4',5,5,5',5'-octamethyl-2,2'-bi(1,3,2-dioxaborolane) (392 mg, 1.544 mmol) and potassium carbonate (350 mg, 3.56 mmol) in dimethylformamide (12 mL) was degassed and flushed with argon gas three times. To this reaction mixture was added [1[1,1'-bis(diphenylphosphino)ferrocene]dichloropalladium (II) (87 mg, 0.119 mmol). The resultant reaction mixture was then heated to 80° C. under a steady stream of argon gas. After 4 hours, the reaction solvent was evaporated under reduced pressure and loaded onto a small pad of CELITE®. The crude reaction mixture was loaded onto a 40 gram silica cartridge and was purified using a ISCO CombiFlash companion flash system. The UV was monitored at 297 nm and the flow rate of this purification was 25 mL/min. The normal phase solvents used were; Solvent A: heptane, Solvent B: ethyl acetate. Using the following gradient method: 0 min-25% B, 50 min-30% B, 60 min-95% B, the purified product eluted between the 25-45 minute marks. Pooled product fractions were evaporated under reduced pressure to give the desired product, (R)-ethyl 1-(4'-(3-methyl-4-(((1-(3-(4,4,5,5-tetramethyl-1,3,2-dioxaborolan-2-yl)phenyl)ethoxy)carbonyl)amino)isoxazol-5-yl)[1,1'-biphenyl]-4-yl)cyclopropanecarboxylate as a white powder (545 mg, 0.852 mmol, 71.7% yield). $^1$H NMR (500 MHz, DMSO-$d_6$) δ 7.80 (m, 4H), 7.66 (d, J=8.3 Hz, 2H), 7.50-7.60 (m, 3H), 7.35-7.47 (m, 3H), 6.03 (br. s, 1H), 5.91 (q, J=6.6 Hz, 1H), 4.14 (q, J=7.1 Hz, 2H), 2.26 (s, 3H), 1.65 (m, 3H), 1.56 (s, 12H), 1.34 (s, 3H), 1.17-1.5 (m, 4H). LCMS m/z (M+H) theory: 637.31, found: 637.25.

C. Synthesis of [$^{11}$C]-(R)-1-(4'-(3-methyl-4-(((1-(m-tolyl)ethoxy)carbonyl)amino)isoxazol-5-yl)-[1,1'-biphenyl]-4-yl)cyclopropanecarboxylic acid

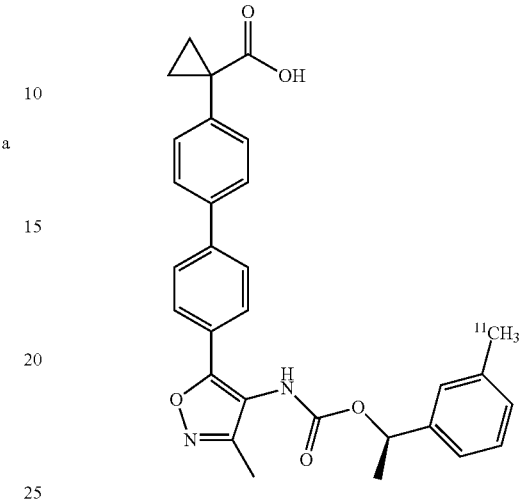

[$^{11}$C]-CO$_2$ was produced via the $^{14}$N(p, α)$^{11}$C nuclear reaction by bombarding a high pressure target containing a mixture of nitrogen with oxygen (0.5-1%) with a proton source using the GE PETtrace cyclotron. The target was irradiated with a proton beam current of 50 μA for 30 min and provides ~3 Ci of [$^{11}$C]-CO$_2$ at the end of bombardment (EOB). The cyclotron produced [$^{11}$C]-CO$_2$ was transferred to lead lined shielded hot cells containing a GE methyl iodide producing module and trapped in a mixture of nickel and molecular sieve. Hydrogen was then passed through the catalyst and reacted with [$^{11}$C]-CO$_2$ at 360° C. to afford [$^{11}$C]-methane, which was subsequently converted to [$^{11}$C]-methyl iodide by reaction with iodine at 720° C. The cross coupling reaction was performed by trapping the [$^{11}$C]-methyl iodide delivered at a rate of 20 mL/min from into a cold solution of the Part B (R)-ethyl 1-(4'-(3-methyl-4-(((1-(3-(4,4,5,5-tetramethyl-1,3,2-dioxaborolan-2-yl)phenyl)ethoxy)carbonyl)amino)isoxazol-5-yl)-[1,1'-biphenyl]-4-yl)cyclopropanecarboxylate (5.2 mg, 8.17 μmol), tetrakis(triphenylphosphine)palladium(0) (0.2 eq.), and cesium carbinate (2.66 mg, 8.17 μmol) in 300 microliters of degassed solution containing 4 parts dimethylformamide: DI water mixture immersed in acetone/ice bath at 0° C. After the radioactivity peaked, the solution mixture was heated at 100° C. for 10 minutes. 0.2 ml of 12 N KOH was added to this reaction mixture to complete the saponification of the ethyl ester. This reaction was heated at 100° C. thermally for 15 minutes. The reaction mixture was then cooled with an ice bath for 1 minute followed the addition of 0.2 12 N HCl to the crude reaction mixture to neutralize the reaction mixture. The resulting mixture was diluted with 2 ml of 75% acetonitrile in 0.1 N ammonium formate. The solution was then injected onto the semi-preparative HPLC column (Gemini C18 5μ, 10×250 mm; 60% MeCN, 0.1 M ammonium formate pH 4.2, 254 nm @ 5 mL/min). [$^{11}$C]-(R)-1-(4'-(3-methyl-4-(((1-(m-tolyl)ethoxy)carbonyl)amino)isoxazol-5-yl)-[1,1'-biphenyl]-4-yl)cyclopropanecarboxylic acid was isolated at the 13.2 minute mark of the HPLC chromatogram. This collected fraction was diluted with 50 ml of 4.2% sodium bicarbonate solution and the entire mixture was transferred to a C18 SEP-PAK®. After the entire solution was transferred, an additional 10 ml of DI water was added to flush the C18 SEP-PAK®. [$^{11}$C]-(R)-1-(4'-(3-Methyl-4-(((1-(m-tolyl)ethoxy)carbonyl)amino)isoxazol-5-yl)-[1,1'-biphenyl]-4-yl)cyclopropanecarboxylic acid was eluted off the C-18 SEP-PAK® with 1 ml of ethanol followed by 3 ml of saline. This solution was then passed through a 0.2μ membrane filter into a sterile product vial that contained 7 ml of saline. Co-injection with cold reference standard (R)-1-(4'-(3-methyl-4-(((1-(m-tolyl)ethoxy)carbonyl)amino)isoxazol-5-yl)-[1,1'-biphenyl]-4-yl)cyclopropanecarboxylic acid confirmed structure using an analytical HPLC Luna C18(2) 5 m 4.6×250 mm 58% MeCN 42% 0.1% ammonium formate pH 4.2. 1.07 GBq (29 mCi) of [$^{11}$C]-(R)-1-(4'-(3-methyl-4-(((1-(m-tolyl)ethoxy)carbonyl)amino)isoxazol-5-yl)-[1,1'-biphenyl]-4-yl)cyclopropanecarboxylic acid was isolated that had a specific activity of 161.7 MBq/nmol (4.38 Ci/mmol) and a radiochemical purity of 98.6%.

Example 2

[$^{11}$C]-(R)-1-(4'-(3-Methyl-4-(((1-(o-tolyl)ethoxy)carbonyl)amino)isoxazol-5-yl)-[1,1'-biphenyl]-4-yl)cyclopropanecarboxylic acid A. Synthesis of (R)-ethyl 1-(4'-(3-methyl-4-(((1-(3-(trimethylstannyl)phenyl)ethoxy)carbonyl)amino)isoxazol-5-yl)-[1,1'-biphenyl]-4-yl)cyclopropanecarboxylate

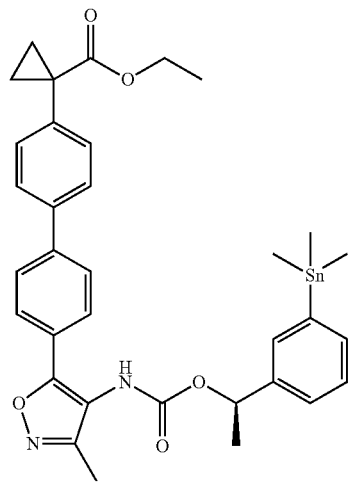

8a

A mixture of (R)-ethyl 1-(4'-(4-(((1-(2-bromophenyl)ethoxy)carbonyl)amino)-3-methylisoxazol-5-yl)-[1,1'-biphenyl]-4-yl)cyclopropanecarboxylate (prepared as described in Example 1, Part A employing (R)-2-bromo-alpha-methylbenzyl alcohol) (100 mg, 0.170 mmol) and tetrakis(triphenylphosphine)palladium (0) (19.60 mg, 0.017 mmol) were dissolved in 1,4-dioxane (2 mL). The crude reaction mixture was degassed and flashed with nitrogen three times before addition of 1,1,1,2,2,2-hexamethyldistannane (66.7 mg, 0.204 mmol). The crude reaction mixture was then heated to 95° C. for 2 hours. After this time, the solvent evaporated under reduced pressure and loaded onto CELITE® cartridge. The crude reaction mixture was purified on ISCO flash separation system. Silica cartridge: 12 g, Solvent A: hexanes, Solvent B: ethyl acetate, monitor at 297 nm, 0 min: 10% ethyl acetate in hexanes, 30 min: 50% ethyl acetate/hexanes mixture, 40 min: 100% ethyl acetate. Pooled product tubes were evaporated under reduced pressure to give 35 mg, (R)-ethyl 1-(4'-(3-methyl-4-(((1-(2-(trimethylstannyl)phenyl)ethoxy)carbonyl)amino)isoxazol-5-yl)-[1,1'-biphenyl]-4-yl)cyclopropanecarboxylate as an off-white solid (35 mg, 0.052 mmol, 30.6% yield). $^1$H NMR (400 MHz, chloroform-d) δ 7.81 (br. s., 2H), 7.64 (d, J=8.3 Hz, 3H), 7.56 (d, J=8.3 Hz, 3H), 7.51-7.34 (m, 5H), 5.81 (br. s., 1H), 4.14 (q, J=7.2 Hz, 2H), 2.25 (s, 3H), 1.69-1.62 (m, 3H), 1.33-1.17 (m, 8H), 0.38 (s, 7H) LCMS (M+H) Theory: 675.18 Found 675.00.

B. [$^{11}$C]-(R)-1-(4'-(3-methyl-4-(((1-(o-tolyl)ethoxy)carbonyl)amino)isoxazol-5-yl)-[1,1'-biphenyl]-4-yl)cyclopropanecarboxylic acid

[$^{11}$C]-CO$_2$ was produced via the $^{14}$N(p, α)$^{11}$C nuclear reaction by bombarding a high pressure target containing a mixture of nitrogen with oxygen (0.5-1%) with a proton source using the GE PETtrace cyclotron. The target was irradiated with a proton beam current of 50 μA for 30 min and provides ~3 Ci of [$^{11}$C]-CO$_2$ at the end of bombardment (EOB). The cyclotron produced [$^{11}$C]-CO$_2$ was transferred to lead lined shielded hot cells containing a GE methyl iodide producing module and trapped in a mixture of nickel and molecular sieve. Hydrogen was then passed through the catalyst and reacted with [$^{11}$C]-CO$_2$ at 360° C. to afford [$^{11}$C]-methane, which was subsequently converted to [$^{11}$C]-methyl iodide by reaction with iodine at 720° C. The $^{11}$C cross coupling reaction was performed by trapping the [$^{11}$C]-methyl iodide delivered at a rate of 20 mL/min from into a solution that contained tris(dibenzylideneacetone)dipalladium (0) (8.5-10 mg) and tri-o-tolylphosphine (9.0-10 mg) in 0.250 ml of dimethyformamide at ambient temperature for 3 minutes. After this time period, a solution of copper chloride (1.4-2.0 mg), potassium carbonate (3-4 mg), and Part A (R)-ethyl 1-(4'-(3-methyl-4-(((1-(3-(trimethylstannyl)phenyl)ethoxy)carbonyl)amino)isoxazol-5-yl)-[1,1'-biphenyl]-4-yl)cyclopropanecarboxylate (8a) (5 mg) was dissolved in 0.250 ml dimethyformamide was transferred into the reaction mixture that contains the mixture of palladium, phosphine and [$^{11}$C]-methyl iodide. This crude reaction mixture was thermally heated at 120° C. for 7 minutes. After this heating period, the reaction was allowed to air cool until the reaction vessel reached 75° C. The crude reaction mixture was the filtered using a ACRODISC® syringe filter 0.45μ, 25 mm nylon membrane filter to filter out all of the palladium from the crude reaction mixture into a container that contained 0.3 ml of 12 N KOH and heated for an additional 7 minutes at 120° C. This reaction mixture was quenched with 0.3 ml of 12 N HCl. The resulting mixture was diluted with 2 ml of 75% acetonitrile in 0.1 N ammonium formate pH 4.2. The solution was then injected onto the semi-preparative HPLC column (ZORBAX® ODS 9.4×250 mm; 55% MeCN, 0.1 M ammonium formate pH 4.2, 254 nm @ 5 mL/min). [$^{11}$C]-(R)-1-(4'-(3-Methyl-4-(((1-(o-tolyl)ethoxy)carbonyl)amino)isoxazol-5-yl)-[1,1'-biphenyl]-4-yl)cyclopropanecarboxylic acid was isolated at the 17.4 minute mark of the HPLC chromatogram. This collected fraction was diluted with 50 ml of 4.2% sodium bicarbonate solution and the entire mixture was transferred to a C18 SEP-PAK®. After the entire solution was transferred an additional 10 ml of DI water was added to flush the C18 SEP-PAK®. [$^{11}$C]-(R)-1-(4'-(3-Methyl-4-(((1-(o-tolyl)ethoxy)carbonyl)amino)isoxazol-5-yl)-[1,1'-biphenyl]-4-yl)

cyclopropanecarboxylic acid was eluted off the C18 SEP-PAK® with 1 ml of ethanol followed by 3 ml of saline. This solution was then passed through a 0.2μ membrane filter into a sterile product vial that contained 7 ml of saline. Co-injection with cold reference standard (R)-1-(4'-(3-methyl-4-(((1-(o-tolyl)ethoxy)carbonyl)amino)isoxazol-5-yl)-[1,1'-biphenyl]-4-yl)cyclopropanecarboxylic acid confirmed structure using an analytical HPLC Luna C18(2) 5 m 4.6×250 mm 58% MeCN 42% 0.1% ammonium formate pH 4.2. 1.35 GBq, (36.6 mCi) of [$^{11}$C]-(R)-1-(4'-(3-methyl-4-(((1-(o-tolyl)ethoxy)carbonyl)amino)isoxazol-5-yl)-[1,1'-biphenyl]-4-yl)cyclopropanecarboxylic acid was isolated with a specific activity of 1.7 MBq/nmol (0.05 Ci/μmol) and a radiochemical purity of 99.5%.

Example 3

A. Synthesis of ethyl 1-(4'-(3-methyl-4-((((3-(tributylstannyl)benzyl)oxy)carbonyl)amino)isoxazol-5-yl)-[1,1'-biphenyl]-4-yl)cyclopropanecarboxylate

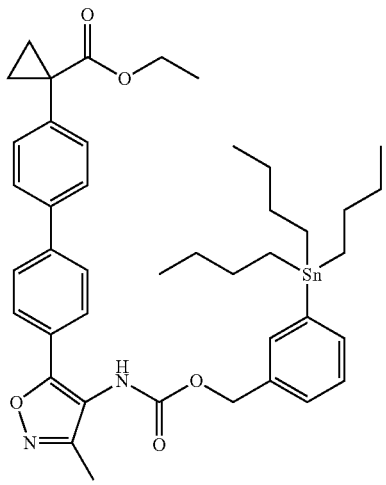

1-(4'-(4-((((3-Bromobenzyl)oxy)carbonyl)amino)-3-methylisoxazol-5-yl)-[1,1'-biphenyl]-4-yl)cyclopropanecarboxylic acid (prepared as described in Example 4, intermediate (15a) (606 mg, 1.028 mmol), 1,1,1,2,2,2-hexabutyldistannane (656 mg, 1.131 mmol) and tetrakis(triphenylphosphine)palladium(0) (119 mg, 0.103 mmol) were degassed and flashed with nitrogen three times. Dioxane (15 mL) was added to this crude reaction mixture and was heated to 95° C. for 15 minutes. The crude reaction mixture was quenched with water and the extracted 2×100 ml of ethyl acetate. The organic layer was dried with sodium sulfate, filtered through CELITE® and concentrated. The crude reaction was purified using flash chromatography (ISCO CombiFlash—eluted with 10-60% EtOAc in hep) to give Part A compound as a sticky/colorless solid. $^1$H NMR (400 MHz, chloroform-d) δ 7.66 (1 H, d, J=8.60 Hz), 7.66 (1 H, d, J=8.60 Hz), 7.57 (1 H, d, J=8.43 Hz), 7.57 (1 H, d, J=8.43 Hz), 7.54 (1 H, d, J=8.60 Hz), 7.54 (1 H, d, J=8.60 Hz), 7.38 (1 H, d, J=8.43 Hz), 7.38 (1 H, d, J=8.43 Hz), 7.28 (1 H, sc, J=6.80 Hz), 7.29 (1 H, sc, J=7.73, 6.80 Hz), 7.28 (1 H, sc, J=7.73 Hz), 7.18 (1 H, s), 5.06 (2 H, s), 4.01 (1 H, sc, J=7.12, −10.69 Hz), 3.95 (1 H, sc, J=7.12, −10.69 Hz), 2.21 (3 H, s), 1.46 (1 H, sc, J=7.88, 7.04, −3.72 Hz), 1.46 (1 H, sc, J=7.88, 7.04, −3.72 Hz), 1.38 (2 H, sc, J=7.85, 7.04 Hz), 1.38 (2 H, sc, J=7.85, 7.04 Hz), 1.38 (2 H, sc, J=7.85, 7.04 Hz), 1.31 (2 H, sc, J=7.85, 7.25 Hz), 1.31 (2 H, sc, J=7.85, 7.25 Hz), 1.31 (2 H, sc, J=7.85, 7.25 Hz), 0.98 (2 H, t, J=7.04 Hz), 0.98 (2 H, t, J=7.04 Hz), 0.98 (2 H, t, J=7.04 Hz), 0.95 (3 H, t, J=7.12 Hz), 0.90 (3 H, t, J=7.25 Hz), 0.90 (3 H, t, J=7.25 Hz), 0.90 (3 H, t, J=7.25 Hz), 0.90 (1 H, sc, J=9.73, 7.04, −3.72 Hz), 0.90 (1 H, sc, J=9.73, 7.04, −3.72 Hz) LCMS (M+H) Theory: 786.6 Found 786.4.

B. Synthesis of [$^{11}$C]-1-(4'-(3-methyl-4-((((3-methylbenzyl)oxy)carbonyl)amino)isoxazol-5-yl)-[1,1'-biphenyl]-4-yl)cyclopropanecarboxylic acid

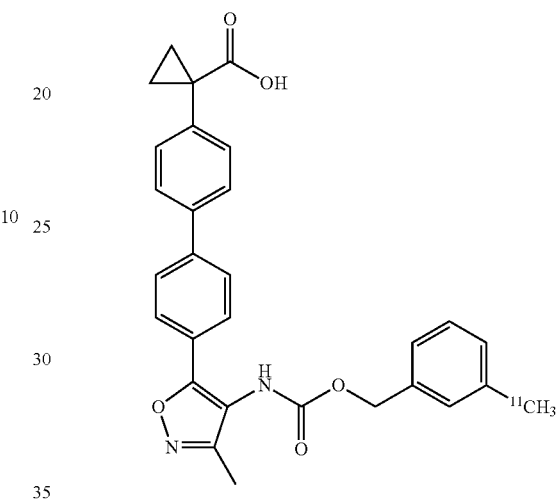

[$^{11}$C]-CO$_2$ was produced via the $^{14}$N(p, α)$^{11}$C nuclear reaction by bombarding a high pressure target containing a mixture of nitrogen with oxygen (0.5-1%) with a proton source using the GE PETtrace cyclotron. The target was irradiated with a proton beam current of 50 μA for 30 min and provides ~3 Ci of [$^{11}$C]-CO$_2$ at the end of bombardment (EOB). The cyclotron produced [$^{11}$C]-CO$_2$ was transferred to lead lined shielded hot cells containing a GE methyl iodide producing module and trapped in a mixture of nickel and molecular sieve. Hydrogen was then passed through the catalyst and reacted with [$^{11}$C]-CO$_2$ at 360° C. to afford [$^{11}$C]-methane, which was subsequently converted to [$^{11}$C]-methyl iodide by reaction with iodine at 720° C. The $^{11}$C cross coupling reaction was performed by trapping the [$^{11}$C]-methyl iodide delivered at a rate of 20 mL/min from into a cold solution that contained tris(dibenzylideneacetone)dipalladium (0) (8.5-10 mg) and tri-o-tolylphosphine (9.0-10 mg) in 0.250 ml of DMF at ambient temperature for 3 minutes. After this time period, a solution of copper chloride (1.4-2.0 mg), potassium carbonate (3-4 mg), and Part A ethyl 1-(4'-(3-methyl-4-(((3-(tributylstannyl)benzyl)oxy)carbonyl)amino)isoxazol-5-yl)-[1,1'-biphenyl]-4-yl)cyclopropanecarboxylate (5 mg) was dissolved in 0.250 ml DMF was transferred into the reaction mixture that contains the palladium, phosphine and [$^{11}$C]-methyl iodide. This crude reaction mixture was heated at 120° C. for 7 minutes. After this heating period, the reaction was allowed to air cool until the reaction vessel reached 75° C. The crude reaction mixture was the filtered using a ACRODISC® syringe filter, 0.45μ 25 mm nylon membrane filter to filter out all of the palladium from the crude reaction mixture into a container that contained 0.3 ml of 12 N KOH and heated for an additional 7 minutes at 120° C. This reaction mixture was quenched with 0.3 ml of 12 N HCl and 2.5 ml of 1% TFA, followed by 1.3 ml of acetonitrile and injected onto the HPLC column and conditions. The compound was purified using a ZORBAX® SB C18 9.6×250 mm 5μ LC column using an isocratic method 56% 0.1% TFA in DI water and 44% 0.1% TFA in acetonitrile while the UV was monitored at 296 nM. This sample was diluted with 50 ml of sterile water for injection and loaded onto to a C-18 SEP-PAK®. The SEP-PAK® was preactivated with 5 ml of ethanol and 10 ml of sterile water for injection. 0.629 GBq (17 mCi) of [$^{11}$C]-1-(4'-(3-methyl-4-(((3-methylbenzyl)oxy)carbonyl)amino)isoxazol-5-yl)-[1,1'-biphenyl]-4-yl)cyclopropanecarboxylic acid was eluted from the C18 SEP-PAK® using 0.5 ml of ethanol, which was added to a 0.2μ filter followed by 4.5 ml of 0.5% sodium bicarbonate solution to give the final formulation. The radiochemical purity was 96% and the specific activity was measured to be 37 MBq/nmol (1.1 Ci/μmol).

Example 4

[$^{18}$F]-1-(4'-((((3-(Fluoromethyl)benzyl)oxy)carbonyl)amino)-3-methylisoxazol-5-yl)-[1,1'-biphenyl]-4-yl)cyclopropanecarboxylic acid A. Synthesis of ethyl 1-(4'-(4-((((3-(hydroxymethyl)benzyl)oxy)carbonyl)amino)-3-methylisoxazol-5-yl)-[1,1'-biphenyl]-4-yl)cyclopropanecarboxylate, Intermediate (12a) (Scheme 5)

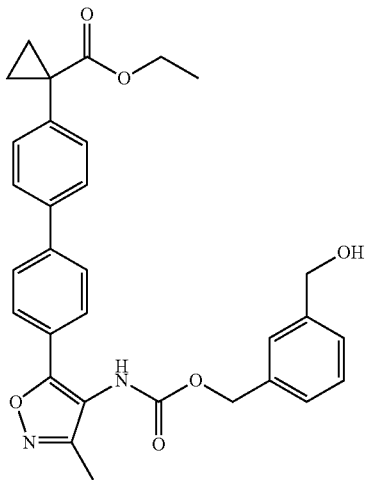

12a

Triethylamine (2.44 mL, 11.25 mmol) was added to a stirring solution of 5-(4'-(1-(ethoxycarbonyl)cyclopropyl)-[1,1'-biphenyl]-4-yl)-3-methylisoxazole-4-carboxylic acid (Intermediate 1a) (4.0 g, 10.23 mmol) in toluene (100 mL) at ambient temperature. Diphenyl phosphoryl azide (2.44 mL, 11.25 mmol) was then added to the resulting reaction mixture and the entire contents were stirred at 85° C. for 15 minutes under a steady stream of nitrogen gas. To this reaction mixture, was added 1,3-phenylenedimethanol (4.24 g, 30.7 mmol) and the resultant reaction mixture was stirred at 80° C. under nitrogen gas for 3 hours. The crude reaction mixture was then concentrated in vacuo at 60° C. to give a light brown oil. The crude reaction mixture was loaded onto a 80 gram silica cartridge and was purified using an ISCO CombiFlash companion flash system. The UV was monitored at 254 nm and the flow rate of this purification was 60 mL/min. The normal phase solvents used were; Solvent A: hexane, Solvent B: ethyl acetate. Using the following gradient method: 0 min-0% B, 15 min-60% B, 20 min-60% B, 30 min-100% B, the purified product eluted between the 10-13 minute marks. Pooled product fractions were evaporated under reduced pressure to give the desired product ethyl 1-(4'-(4-((((3-(hydroxymethyl)benzyl)oxy)carbonyl)amino)-3-methylisoxazol-5-yl)-[1,1'-biphenyl]-4-yl)cyclopropanecarboxylate as a colorless solid (12a) (3.23 g, 6.14 mmol, 60.0% yield). $^1$H NMR (400 MHz, chloroform-d) δ 7.80 (br. s, 2H), 7.66 (d, J=8.4 Hz, 2H), 7.63-7.51 (m, 3H), 7.51-7.41 (m, 3H), 6.12 (br. s, 1H), 5.84 (br. s, 1H), 4.14 (q, J=7.0 Hz, 2H), 2.26 (s, 3H), 1.70-1.63 (m, 3H), 1.61 (s, 3H), 1.26-1.17 (m, 5H). LCMS m/z (M+H) theory: 527.21 found: 527.15.

B. Synthesis of ethyl 1-(4'-(4-((((3-(bromomethyl)benzyl)oxy)carbonyl)(tert-butoxycarbonyl)amino)-3-methylisoxazol-5-yl)-[1,1'-biphenyl]-4-yl)cyclopropanecarboxylate

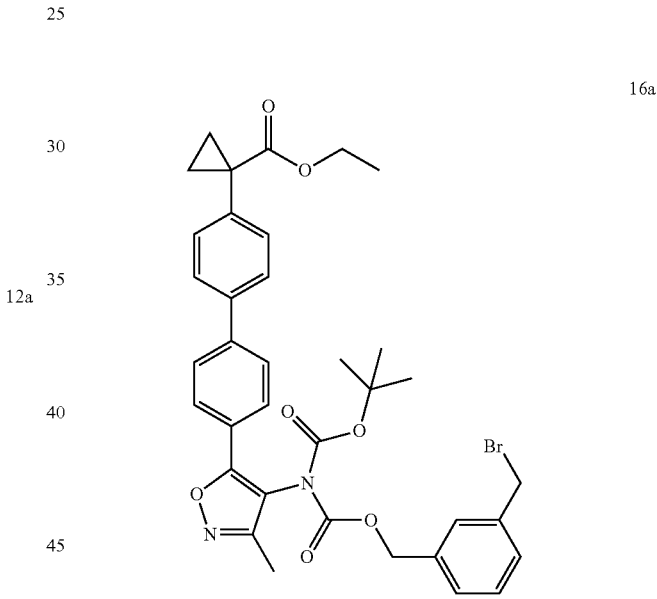

16a

Ethyl 1-(4'-(4-((((3-(hydroxymethyl)benzyl)oxy)carbonyl)amino)-3-methylisoxazol-5-yl)-[1,1'-biphenyl]-4-yl)cyclopropanecarboxylate (Intermediate 12a) (156 mg, 0.296 mmol) was dissolved in dimethoxyethane (3 mL). To this stirring solution was added phosphorus tribromide (0.035 mL, 0.370 mmol). The reaction mixture was stirred at ambient temperature for 90 minutes TLC (40% EtOAc in hex) suggested a total conversion. The crude reaction mixture was flushed through a bed of silica gel and was concentrated in vacuo to give a colorless solid. To a stirring solution of ethyl 1-(4'-(4-((((3-(bromomethyl)benzyl)oxy)carbonyl)amino)-3-methylisoxazol-5-yl)-[1,1'-biphenyl]-4-yl)cyclopropanecarboxylate (Intermediate 15a) (100 mg, 0.170 mmol) in dichloromethane (DCM, 1 mL) was sequentially added N,N-diisopropylethylamine (DIPEA, 0.074 mL, 0.424 mmol), di-tert-butyl dicarbonate (0.059 mL, 0.254 mmol), and 4-dimethylaminopyridine (DMAP, 2.072 mg, 0.017 mmol). This reaction was allowed to stir at ambient temperature and was monitored via TLC, after 15 minutes.

TLC (40% EtOAc in hex) suggested a complete conversion (Rf~0.5). The crude reaction mixture was concentrated in vacuo and purified using flash chromatography (ISCO CombiFlash—eluted with 5-60% EtOAc in hep) to give Intermediate 16a as a sticky/colorless solid. $^1$H NMR (500 MHz, chloroform-d) d 7.77-7.72 (m, 2H), 7.70-7.65 (m, 2H), 7.61-7.56 (m, 2H), 7.51-7.44 (m, 2H), 7.32-7.26 (m, 4H), 7.26-7.20 (m, 2H), 7.12 (d, J=7.8 Hz, 1H), 5.20 (d, J=1.7 Hz, 1H), 4.41-4.34 (m, 2H), 4.16 (q, J=7.2 Hz, 2H), 2.21-2.15 (m, 2H), 1.70-1.65 (m, 2H), 1.57 (s, 3H), 1.42-1.33 (m, 8H), 1.28-1.19 (m, 4H). LCMS (M+H) Theory 691.18 Found 691.21.

C. Synthesis of [$^{18}$F]-1-(4'-(4-((((3-(fluoromethyl)benzyl)oxy)carbonyl)amino)-3-methylisoxazol-5-yl)-[1,1'-biphenyl]-4-yl)cyclopropanecarboxylic acid

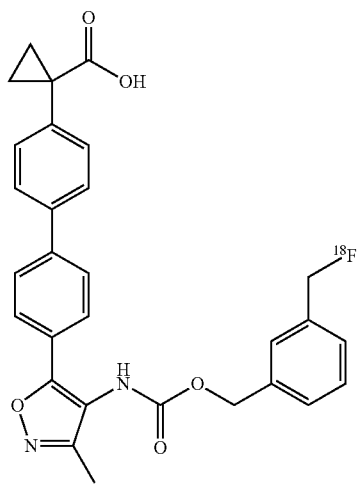 [SMILES: Cc1noc(-c2ccc(-c3ccc(C4(C(=O)O)CC4)cc3)cc2)c1NC(=O)OCc1cccc(C[18F])c1]

A 1.5 ml, 25.9 GBq (700 mCi) sample of F-18 fluoride was produced via the $^{18}$O (p, n)$^{18}$F nuclear reaction by bombarding a liquid target containing an $^{18}$O enriched water with a proton source using a Siemens eclipse cyclotron and purchased from Siemens molecular imaging in North Wales, Pa. This sample was delivered directly into a vial that contained 4,7,13,16,21,24-hexaoxa-1,10-diazabicyclo[8.8.8]hexacosane (2.7 mg, 7.17 μmol) and potassium carbonate (2.5 mg, 0.018 mmol) and acetonitrile (2 ml). This 3.5 ml solution was then azeotropically dried. This process was completed by applying a gentle stream of $N_2$ using and partial vacuum. When the volume of the liquid was reduced to less than 0.3 ml, a 1 ml aliquot of acetonitrile was added and reduced by azeotropic distillation. This process was repeated 5 times in an effort to remove all traces of water. After this process was completed, the cryptand was further dried under full vacuum for 20 minutes. To the dried cryptan salt was added ethyl 1-(4'-(4-((((3-(bromomethyl)benzyl)oxy)carbonyl)(tert-butoxycarbonyl)amino)-3-methylisoxazol-5-yl)-[1,1'-biphenyl]-4-yl)cyclopropanecarboxylate (10 mg, 0.015 mmol) that was dissolved in a mixture of acetonitrile and 1-butyl-3-methyl-1H-imidazol-3-ium hexafluorophosphate(V) (3.30 mg, 0.012 mmol). A stock solution of 1-butyl-3-methyl-1H-imidazol-3-ium hexafluorophosphate(V) (3.30 mg, 0.012 mmol) was prepared by weighing out 66 mg of the ionic liquid in 6.6 ml of acetonitrile and taking 0.3 ml of this stock solution to dissolve the boc protected precursor. This crude reaction mixture was heated at 68° C. for 45 minutes. Upon completion of heating, the crude reaction mixture was cooled to 45° C. and diluted with 4 ml of dichloromethane. This mixture was applied to a silica SEP-PAK® cartridge into a container that contained 0.3 ml of concentrated TFA. The dichloromethane was concentrated until 0.6 ml of the crude reaction solution remained. This 0.6 ml solution was heated at 68° C. for 10 minutes. To this reaction mixture, was added 0.6 ml of 50% wt NaOH and 0.3 ml of dioxane and the reaction was heated at 68° C. for an additional 15 minutes. To this reaction mixture was added 1 ml of concentrated HCl dissolved in 1 ml 0.1% TFA and an additional 1.5 ml of MeCN (0.1% TFA) was added to the reaction mixture. The compound was purified using a ZORBAX® SB C18 9.6×250 mm 5μ LC column and a gradient method from 50% 0.1% TFA in DI water and 50% 0.1% TFA in acetonitrile to a 40% 0.1% TFA in DI water and 60% 0.1% TFA in acetonitrile over a 25 minute period while the UV was monitored at 296 nM. 1.11 GBq, (30 mCi) of [$^{18}$F]-1-(4'-(4-((((3-(fluoromethyl)benzyl)oxy)carbonyl)amino)-3-methylisoxazol-5-yl)-[1,1'-biphenyl]-4-yl)cyclopropanecarboxylic acid was isolated between the 14 and 17 minute mark of the chromatogram. This sample was diluted with 50 ml of sterile water for injection and loaded onto a C-18 SEP-PAK® cartridge and eluted from this SEP-PAK® using 1 ml of ethanol, which was added to 10 ml of saline for injection and filtered through a 0.2μ filter to give the final Example 4 compound. The radiochemical purity was 99.2% and specific activity was measured to be 114.3 GBq/nmol (3.09 Ci/μmol).

Example 5

[$^{11}$C]-(R)-1-(4'-(3-Methyl-4-(((1-(p-tolyl)ethoxy)carbonyl)amino)isoxazol-5-yl)-[1,1'-biphenyl]-4-yl)cyclopropanecarboxylic acid

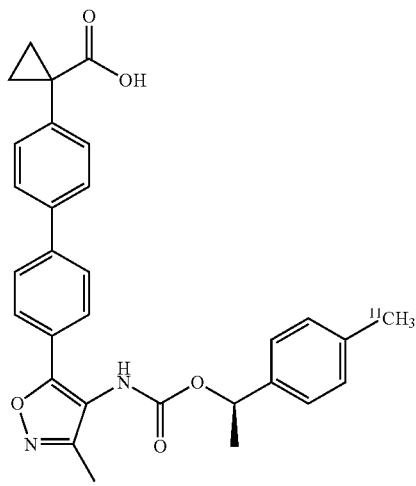 [SMILES: Cc1noc(-c2ccc(-c3ccc(C4(C(=O)O)CC4)cc3)cc2)c1NC(=O)O[C@H](C)c1ccc([11CH3])cc1]

Following the procedures of Example 1 except substituting (R)-4-bromo-alpha-methylbenzyl alcohol for (R)-3-bromo-alpha-methylbenzyl alcohol, the title compound was obtained.

Example 6

[$^{18}$F]-(R)-1-(4'-(((3-(Fluoromethyl)phenyl)ethoxy)carbonyl)amino)-3-methyl)isoxazole-5-yl)-[1,1'-biphenyl]-4-yl)cyclopropanecarboxylic acid

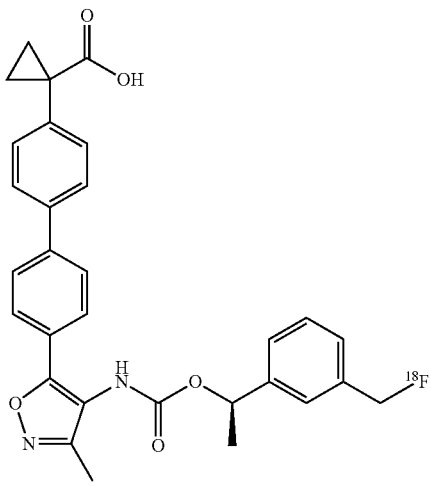 [SMILES: Cc1noc(-c2ccc(-c3ccc(C4(C(=O)O)CC4)cc3)cc2)c1NC(=O)O[C@H](C)c1cccc(C[18F])c1]

Following the procedure of Example 4 except substituting 1-(3-(hydroxymethyl)phenyl)ethanol for 1,3-phenylenedimethanol, the title compound was obtained.

Example 7

[$^{18}$F]-(R)-Ethyl 1-(4'-(4-(((1-(3-(fluoromethyl)phenyl)ethoxy)carbonyl)amino)-3-methylisoxazol-5-yl)-[1,1'-biphenyl]-4-yl)cyclopropanecarboxylate

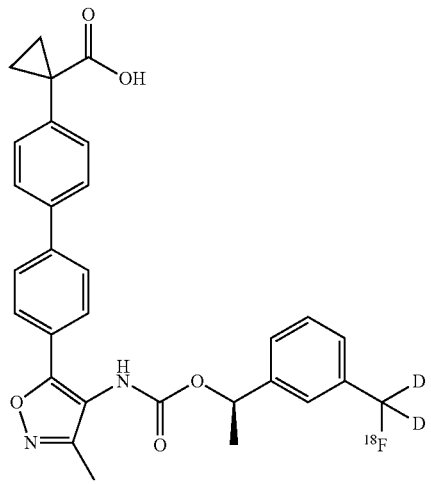 [SMILES: [2H]C([2H])([18F])c1cccc([C@@H](C)OC(=O)Nc2c(C)noc2-c2ccc(-c3ccc(C4(C(=O)O)CC4)cc3)cc2)c1]

(R)-1-(3-Bromophenyl)ethanol and 2,4,6-tri(methyl-d$_3$)-1,3,5,2,4,6-trioxatriborinane (commercially available) are dissolved in a mixture of toluene and water. Potassium carbonate and 1,1'-bis(diphenylphosphino)ferrocene palladium(II) dichloride dichloromethane complex is added to this reaction mixture. The reaction mixture is refluxed 110° C. with stirring for 3 hours. The reaction is then cooled to room temperature, washed with water and brine. The reaction mixture is dried with sodium sulfate, filtered, concentrated and purified using normal phase silica gel chromatography to afford (R)-1-(m-tolyl)ethanol-d$_3$.

(R)-1-(m-Tolyl)ethanol-d$_3$ is then dissolved in a mixture of carbon tetrachloride and N-bromosuccinimide. This reaction stirs for 24 hours. To this reaction is added water and the reaction is extracted further with ethyl acetate, washed with brine, dried with sodium sulfate and concentrated. The crude reaction mixture is purified using normal phase silica gel chromatography affording (R)-3-bromo-alpha-methylbenzyl alcohol-d$_2$. Triethylamine is added to a stirring solution of 5-(4'-(1-(ethoxycarbonyl)cyclopropyl)-[1,1'-biphenyl]-4-yl)-3-methylisoxazole-4-carboxylic acid in toluene at ambient temperature. Diphenyl phosphoryl azide is added to the resulting reaction mixture and the entire contents are stirred at 80° C. for 15 minutes under a steady stream of nitrogen gas. To this reaction mixture, (R)-3-bromo-alpha-methylbenzyl alcohol-d$_2$ is added and the resulting reaction mixture is stirred at 80° C. under nitrogen gas for 17 hours. The crude reaction mixture is concentrated in vacuo at 60° C. and purified using normal phase silica gel chromatography to give the desired product (R)-ethyl 1-(4'-(4-(((1-(3-(bromomethyl-d$_2$)phenyl)ethoxy)carbonyl)amino)-3-methylisoxazol-5-yl)-[1,1'-biphenyl]-4-yl)cyclopropanecarboxylate (18a).

N,N-Diisopropylethylamine, di-tert-butyl dicarbonate and 4-dimethylaminopyridine are combined with a stirring solution of (R)-ethyl 1-(4'-(4-((((1-(3-(bromomethyl-d$_2$)phenyl)ethoxy)carbonyl)amino)-3-methylisoxazol-5-yl)-[1,1'-biphenyl]-4-yl)cyclopropanecarboxylate in dichloromethane. This reaction mixture stirs at ambient temperature for 1 hour. The crude reaction mixture is concentrated in vacuo and purified using normal phase silica gel chromatography affording (R)-ethyl 1-(4'-(4-((((1-3-(bromomethyl-d$_2$)phenyl)ethoxy)carbonyl)(tert-butoxycarbonyl)amino)-3-methylisoxazol-5-yl)-[1,1'-biphenyl]-4-yl)cyclopropanecarboxylate (19a).

F-18 fluoride is delivered directly into a vial that contained 4,7,13,16,21,24-hexaoxa-1,10-diazabicyclo[8.8.8]hexacosane and potassium carbonate and acetonitrile. This 3.5 ml solution is azeotropically dried in an effort to remove all traces of water. This reaction mixture is further dried under full vacuum. To the dried cryptan salt is added (R)-ethyl 1-(4'-(4-((((1-3-(bromomethyl-d$_2$)phenyl)ethoxy)carbonyl)(tert-butoxycarbonyl)amino)-3-methylisoxazol-5-yl)-[1,1'-biphenyl]-4-yl)cyclopropanecarboxylate which is dissolved in a mixture of acetonitrile and 1-butyl-3-methyl-1H-imidazol-3-ium hexafluorophosphate(V) This reaction mixture is heated at 68° C. for 45 minutes, cooled to 45° C. and diluted with 4 ml of dichloromethane. This mixture is applied to a silica SEP-PAK® cartridge into a container that contains concentrated TFA. The dichloromethane was concentrated and is heated at 68° C. for 10 minutes. To this reaction mixture is added 12 N NaOH and dioxane and the reaction heats at 68° C. for 15 minutes. Concentrated HCl is added to this reaction mixture and crude reaction is purified using a reverse phase HPLC column chromatography affording [$^{18}$F]-(R)-ethyl 1-(4'-(4-(((1-(3-(fluoromethyl)phenyl)ethoxy)carbonyl)amino)-3-methylisoxazol-5-yl)-[1,1'-biphenyl]-4-yl)cyclopropanecarboxylate

Example 8

[¹¹C]-(R)-1-(4'-(3-Methyl-4-(((1-(o-tolyl)ethoxy)carbonyl)amino)isoxazol-5-yl)-[1,1'-biphenyl]-4-yl)cyclopropanecarboxylic acid

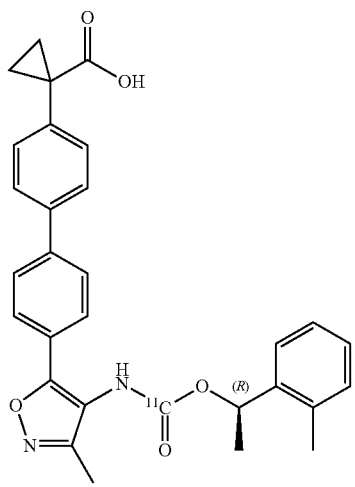

Triethylamine stirs with a solution of (R)-1-(o-tolyl)ethanol that is dissolved in dichloromethane. Mesylchloride is added to this solution and the reaction stirs for 12 hours. This crude reaction is purified using normal phase silica gel chromatography generating (R)-1-(o-tolyl)ethyl methanesulfonate. Separate solutions of (R)-1-(o-tolyl)ethyl methanesulfonate, ethyl 1-(4'-(4-amino-3-methylisoxazol-5-yl)-[1,1'-biphenyl]-4-yl)cyclopropanecarboxylate (21a) (prepared as described in WO 2012/138797) and DBU are dissolved in DMF (which are sparged with helium gas to remove any $^{12}CO_2$ from the atmosphere). Equal volumes of these solutions are combined in a reaction vessel, which is septum sealed. The resulting solution is sparged with helium gas for 2-3 min. [¹¹C]-Carbon dioxide is bubbled into this solution at 20 ml/min from the target of a cyclotron and introduced into the reaction solution under constant flow at room temperature. The reaction vessel is sealed upon removing the inlet and outlet needles and the reaction heats at 75° C. for 10 minutes. 12 N KOH is added to the crude reaction mixture and the resulting mixture heats at 75° C. for 15 minutes. The solution is acidified with 12 N HCl and the residual $^{11}CO_2$ trapped in solution is removed from the solution by sparging with a stream of helium gas. The crude reaction is purified via reverse phase HPLC to afford [¹¹C]-(R)-1-(4'-(3-methyl-4-(((1-(o-tolyl)ethoxy)carbonyl)amino)isoxazol-5-yl)-[1,1'-biphenyl]-4-yl)cyclopropanecarboxylic acid.

Example 9

In vitro autoradiography with [¹⁸F]-1-(4'-(4-((((3-(fluoromethyl)benzyl)oxy)carbonyl)amino)-3-methylisoxazol-5-yl)-[1,1'-biphenyl]-4-yl)cyclopropanecarboxylic acid The naïve lung mouse tissues were collected from female C57BL/6 mice (8-10 weeks old; 18-25 grams), the samples were stored in −80° C. degree freezer until use. The bleomycin treated animals consists of female C57BL/6 mice (8-10 weeks old; 18-25 grams) were anesthetized with 5% isoflurane the day before study initiation. Bleomycin was dissolved into sterile phosphate buffered saline to a concentration of 500 μg/ml. For injection, mice were anesthetized with 5% isoflurane and using a 1 cc syringe with a 27 g needle, 100 μl of the stock bleomycin solution was injected subcutaneously (SC) into the center of each shaved region (50 μg/site). The bleomycin was administered 5 days/week, Monday through Friday, and was injected into the same region each day until Day 28. Specifically the left lobe of lung was harvested and inflated using a 1:1 OCT (which consists of a mixture 10.24% w/w polyvinyl alcohol 4.26% w/w polyethylene glycol 85.50 w/w non-reactive ingredients)/phosphate buffered saline mixture.

Fresh tissues from naïve mouse lungs and bleomycin treated lungs were immersed into OCT and chilled in 2-methylbutane for 2-5 minutes until frozen. The tissues were then wrapped in foil/ZIPLOC® bag and stored at −80° C. Tissue sections of 10 μm thickness (collected as 2 sections/slide) were cut using a cryostat and thaw-mounted on glass microscope slides, allowed to air dry for approximately 30 minutes. Blocking studies with 1-(4'-(3-methyl-4-(((1-phenylethoxy)carbonyl)amino)isoxazol-5-yl)-[1,1'-biphenyl]-4-yl)cyclopropanecarboxylic acid at 0.1 nM, 1 nM and 10 nM respectively were conducted using the following conditions. The individual slides, 4 slides per concentration, were pre-incubated in a mixture of 50 mM Hepes, 100 nM NaCl, pH=7.4 and 0.05% Tween-20 buffer solution that contains only this buffer (total binding), as well as 0.1 M 1-(4'-(3-methyl-4-(((1-phenylethoxy)carbonyl)amino)isoxazol-5-yl)-[1,1'-biphenyl]-4-yl)cyclopropanecarboxylic acid, 1 nM 1-(4'-(3-methyl-4-(((1-phenylethoxy)carbonyl)amino)isoxazol-5-yl)-[1,1'-biphenyl]-4-yl)cyclopropanecarboxylic acid and 10 nM 1-(4'-(3-methyl-4-(((1-phenylethoxy)carbonyl)amino)isoxazol-5-yl)-[1,1'-biphenyl]-4-yl)cyclopropanecarboxylic acid for a 3 hour period. These individual slides were then incubated in the buffer solution containing 3.9 nM of [¹⁸F]-1-(4'-(4-((((3-(fluoromethyl)benzyl)oxy)carbonyl)amino)-3-methylisoxazol-5-yl)-[1,1'-biphenyl]-4-yl)cyclopropanecarboxylic acid that was formulated in 10% ethanol 90% 0.5% sodium bicarbonate. This solution was diluted with 300 ml of buffer solution to generate a stock solution. From this stock solution, 40 ml was added to each incubation chamber. One of these chambers contained only the radioligand buffer solution, which is referred to as the total binding section. An additional 40 ml was added to each incubation chamber along with the relevant concentration of blocking compound (1-(4'-(3-methyl-4-(((1-phenylethoxy)carbonyl)amino)isoxazol-5-yl)-[1,1'-biphenyl]-4-yl)cyclopropanecarboxylic acid at 0.1 nM, 1 nM, 10 nM). Then the individual slides were incubated in the buffer solution containing the [¹⁸F]-1-(4'-(4-((((3-(fluoromethyl)benzyl)oxy)carbonyl)amino)-3-methylisoxazol-5-yl)-[1,1'-biphenyl]-4-yl)cyclopropanecarboxylic acid radioligand and blocking compound for 1.5 hours at room temperature to reach maximum binding. After 4.5 hours of total incubation, slides from each treatment group were removed from the incubation solutions and placed in an ice-cold wash buffer (50 mM Hepes, 100 mM NaCl, and 0.05% Tween-20, pH=7.4) and rinsed 4 times. Slides were then dried under a stream of cold air for approximately 1 hour. The air-dried slides were exposed by placing the slides onto an imaging plate (BAS-SR 3545S) for 15 minutes at room temperature. The imaging plate was scanned using the bioimaging analyzer (Fujifilm Fluorescent Image Analyzer, FLA-9000). The pixel size of the autoradiogram images was 100 μm. Image analysis was performed using the Multi-Gauge software. The regions of interest (ROIs) were drawn to surround the entire lung area in all study groups. Then percentage of displacement was calculated from the total binding value and the non-specific binding values. Upon completion of the autoradiography analysis, the total binding lung tissue slides from this study were stained for collagen using H&E and Masson's Trichrome stain. The staining study was previously described (Swaney, J. S. et al., *British Journal of Pharmacology*, 160:1699-1713 (2010)).

Figure 2:
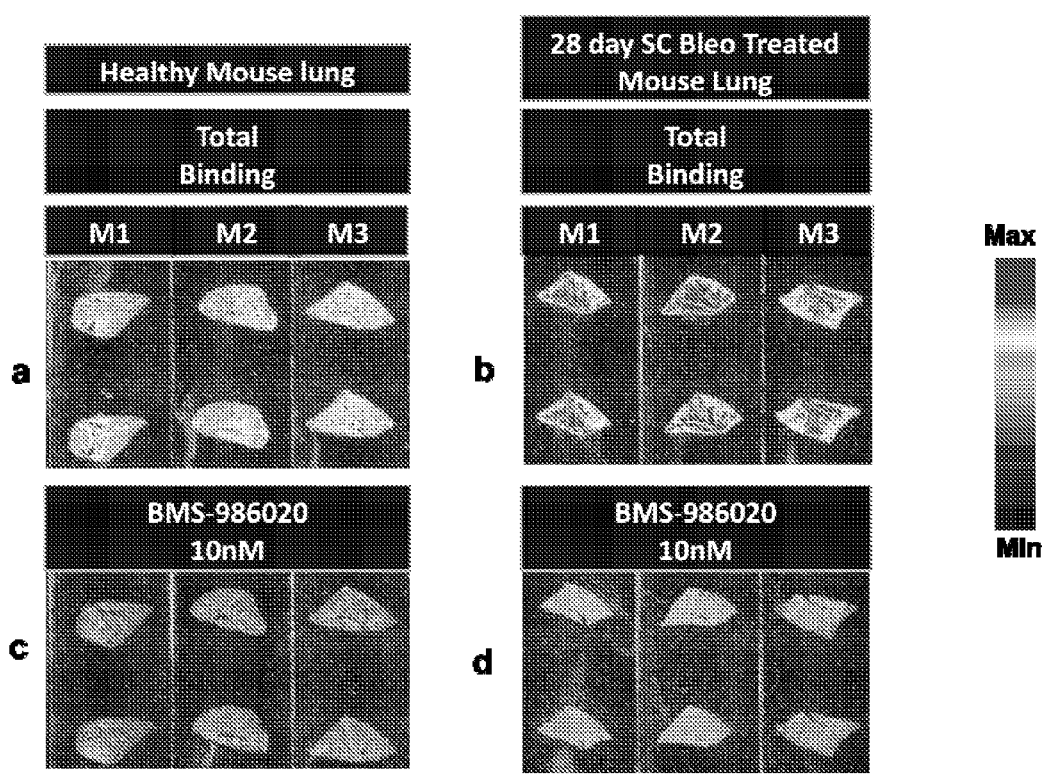
FIG. 2 shows a 10 μm thick lung tissue slices from naïve (healthy) mouse sections and bleomycin treated mouse lung sections that have been imaged using autoradiography. a) total radioligand binding in naïve mouse lung sections b) total radioligand binding in bleomycin treated mouse lung sections c) radioligand displacement with 10 nM 1-(4'-(3-methyl-4-(((1-phenylethoxy)carbonyl)amino)isoxazol-5-yl)-[1,1'-biphenyl]-4-yl)cyclopropanecarboxylic acid in naïve mouse lung sections d) radioligand displacement with 10 nM 1-(4'-(3-methyl-4-(((1-phenylethoxy)carbonyl)amino)isoxazol-5-yl)-[1,1'-biphenyl]-4-yl)cyclopropanecarboxylic acid in bleomycin treated mouse lung sections. M1, M2, M3 represent lung sections from 3 separate mice. This figure shows a ~3 fold increase in radioligand binding in the disease induced animals and ~80% radioligand displacement using 10 nM 1-(4'-(3-methyl-4-(((1-phenylethoxy)carbonyl)amino)isoxazol-5-yl)-[1,1'-biphenyl]-4-yl)cyclopropanecarboxylic acid.

The apparent displacement of the [$^{18}$F]-1-(4'-(4-((((3-(fluoromethyl)benzyl)oxy)carbonyl)amino)-3-methylisoxazol-5-yl)-[1,1'-biphenyl]-4-yl)cyclopropanecarboxylic acid radioligand when compared to the total binding sections was determined for 3 different concentrations 0.1 nM, 1 nM and 10 nM 1-(4'-(3-methyl-4-(((1-phenylethoxy)carbonyl)amino)isoxazol-5-yl)-[1,1'-biphenyl]-4-yl)cyclopropanecarboxylic acid in both naïve and bleomycin mouse lung sections. A dose dependent displacement of [$^{18}$F]-1-(4'-(4-((((3-(fluoromethyl)benzyl)oxy)carbonyl)amino)-3-methyl-isoxazol-5-yl)-[1,1'-biphenyl]-4-yl)cyclopropanecarboxylic acid was seen in both naïve mouse lung tissue sections 0.1 nM 1-(4'-(3-methyl-4-(((1-phenylethoxy)carbonyl)amino)isoxazol-5-yl)-[1,1'-biphenyl]-4-yl)cyclopropanecarboxylic acid 18.2+/−7.6%, 1 nM 1-(4'-(3-methyl-4-(((1-phenylethoxy)carbonyl)amino)isoxazol-5-yl)-[1,1'-biphenyl]-4-yl)cyclopropanecarboxylic acid 57.3+/−2.6%, 10 nM 1-(4'-(3-methyl-4-(((1-phenylethoxy)carbonyl)amino)isoxazol-5-yl)-[1,1'-biphenyl]-4-yl)cyclopropanecarboxylic acid 72.6%+/−6.7%. A similar result was shown in bleomycin treated mouse lung tissues (surrogate for lung fibrosis in the mouse model) sections 0.1 nM 1-(4'-(3-methyl-4-(((1-phenylethoxy)carbonyl)amino)isoxazol-5-yl)-[1,1'-biphenyl]-4-yl)cyclopropanecarboxylic acid 11.3+/−4.2%, 1 nM 1-(4'-(3-methyl-4-(((1-phenylethoxy)carbonyl)amino)isoxazol-5-yl)-[1,1'-biphenyl]-4-yl)cyclopropanecarboxylic acid 55.5+/−2.3%, 10 nM 1-(4'-(3-methyl-4-(((1-phenylethoxy)carbonyl)amino)isoxazol-5-yl)-[1,1'-biphenyl]-4-yl)cyclopropanecarboxylic acid 82.7%+/−1.4%. The [$^{18}$F]-1-(4'-(4-((((3-(fluoromethyl)benzyl)oxy)carbonyl)amino)-3-methylisoxazol-5-yl)-[1,1'-biphenyl]-4-yl) cyclopropanecarboxylic acid binding to the lung resides within positive collagen as shown in FIG. 1. A three-fold increase in radioligand binding was shown in bleomycin treated mouse lung sections when compared to naïve mouse lung tissues as shown in FIG. 2.

Together, these results provide direct visualization of the LPA1 receptor in lung tissue in both healthy and bleomycin treated mice. In addition, the dose dependent blockade of the receptor with a potent and specific LPA1 antagonist, further validates the use of [$^{18}$F]-1-(4'-(4-((((3-(fluoromethyl)benzyl)oxy)carbonyl)amino)-3-methylisoxazol-5-yl)[1,1'-biphenyl]-4-yl)cyclopropanecarboxylic acid and structurally related compounds for PET imaging.

Overall these ex-vivo autoradiography studies support the use of [$^{18}$F]-1-(4'-(4-((((3-(fluoromethyl)benzyl)oxy)carbonyl)amino)-3-methylisoxazol-5-yl)-[1,1'-biphenyl]-4-yl)cyclopropanecarboxylic acid and related structures as PET radioligands for the determination of LPA1 target engagement and dose/receptor occupancy relationships with LPA1 antagonists.

FIG. 1 shows a 10 μm thick lung tissue slice that has been imaged using autoradiography to determine LPA1 receptor binding in a bleomycin treated mouse (model for lung fibrosis). This same tissue section was stained for collagen (trichrome staining) to confirm that the radioligand binds in areas consistent with collagen expression.

FIG. 2 shows a 10 μm thick lung tissue slices from naïve (healthy) mouse sections and bleomycin treated mouse lung sections that have been imaged using autoradiography.
  (a) total radioligand binding in naïve mouse lung sections
  (b) total radioligand binding in bleomycin treated mouse lung sections
  (c) radioligand displacement with 10 nM 1-(4'-(3-methyl-4-(((1-phenylethoxy)carbonyl)amino)isoxazol-5-yl)-[1,1'-biphenyl]-4-yl)cyclopropanecarboxylic acid in naïve mouse lung sections d) radioligand displacement with 10 nM 1-(4'-(3-methyl-4-(((1-phenylethoxy)carbonyl)amino)isoxazol-5-yl)-[1,1'-biphenyl]-4-yl)cyclopropanecarboxylic acid in bleomycin treated mouse lung sections. M1, M2, M3 represent lung sections from 3 separate mice. This figure shows a ~3 fold increase in radioligand binding in the disease induced animals and ~80% radioligand displacement using 10 nM 1-(4'-(3-methyl-4-(((1-phenylethoxy)carbonyl)amino)isoxazol-5-yl)[1,1'-biphenyl]-4-yl)cyclopropanecarboxylic acid.

Example 10

Test-Retest and Saturation Studies of the LPA1 Radioligand [$^{11}$C]-BMT-136088 ([11C]-(R)-1-(4'-(3-Methyl-4-(((1-(m-tolyl)ethoxy)carbonyl)amino) isooxazol-5-yl)-[1,1'-biphenyl]-4-yl)cyclopropanecarboxylic acid The following terminology is employed to identify compounds used in this study.

The term "[$^{11}$C]-BMT-136088" as employed hereinafter refers to the [$^{11}$C]-radiolabeled compound prepared in Example 1.

The term "BMS-986020" as employed hereinafter refers to the compound prepared in Example 1 of U.S. Pat. No. 8,058,300.

Study Objectives

This study was divided in two parts: First, the test-retest variability of [$^{11}$C]-BMT-136088 binding in a within-day protocol. Second, a saturation study was performed to evaluate the fraction of specific and non-specific binding for the radiotracer [$^{11}$C]-BMT-136088, the in vivo equilibrium dissociation constant $K_D$, and the radiopharmaceutical tracer-dose limit (to achieve less than 5% self-occupancy).

Some of the data from a previous tracer exploration study, including blocking study data for the unlabeled compound, BMS-986020, having the following structure:

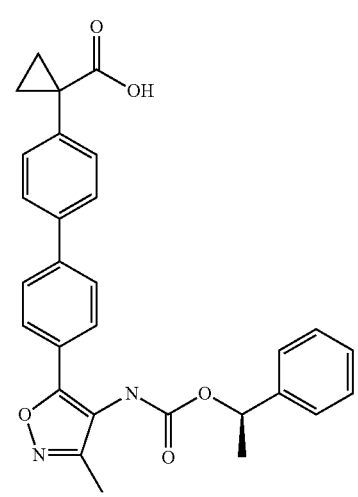

B were also re-analyzed with the methods described here to verify previous conclusions and ensure consistency of method.

1. Study Design a) BMS-986020 Blocking Study

For the blocking data reanalyzed here, each animal was scanned twice during the administration of [$^{11}$C]-BMT-136088, using a bolus plus infusion (B+I) protocol: at baseline first, then during the administration of the blocking drug, BMS-986020, also using a bolus plus infusion protocol.

b) Test-Retest Study

In the test-retest study, each animal was scanned twice per day, with the same interval between the two scans as in the blocking study, to measure the variability of [$^{11}$C]-BMT-136088 binding parameter and assess if there was a systematic difference in binding parameters between the two scan times (for example due to the prolonged anesthesia). The study was performed in the same animals as the blocking study.

c) Saturation Study

In the saturation study, each animal was scanned twice a day, with varying mass of [$^{11}$C]-BMT-136088, from tracer dose to near-saturating doses. The interval between the two scans was the same as in the blocking study and test-retest study. For the first scans, tracer doses were used in 3 out of 4 study days. On the fourth day, the first scan dose was not performed at tracer dose, but the mass of the first dose scan was substantially lower than the second dose to minimize the influence of the first injection on the second scan data.

2. Study Drug, Dosage, and Administration

In the blocking study, BMS-986020 was administered i.v. using a 10-min bolus (0.25 mg/kg/hr) followed by a ~230 min infusion (0.25 mg/kg/hr) for a total dose of 1.224±0.015 mg/kg.

3. Study Population

Two rhesus monkeys were included in the blocking, test-retest, and saturation studies: one male, one female; age=4.8±0.8 y; weight=8.6±0.4 kg. Studies in the same animal were separated by at least 2 weeks to allow the animal to recover from anesthesia and other effects. Four rhesus monkeys (2M, 2F) were included in the dosimetry study.

4. PET Imaging Parameters

Following a low-dose, CT scan used for attenuation correction and to delineate the lung regions of interest, [$^{11}$C]-BMT-136088 was injected using a computer-control pump with a bolus plus infusion protocol, with an initial 1-min bolus and a ~119-min infusion. The volume injected during the initial bolus represented 100 min (Kbol) worth of infusion in the blocking and test-retest study, and 300 min worth of infusion in the saturation study.

The mean±SD of the specific activity (SA) at the end of synthesis (EOS) was 426±178 MBq/nmol (n=16), and 228±97 MBq/nmol (n=16) at the time of injection (TOI; not including unlabeled BMT-136088

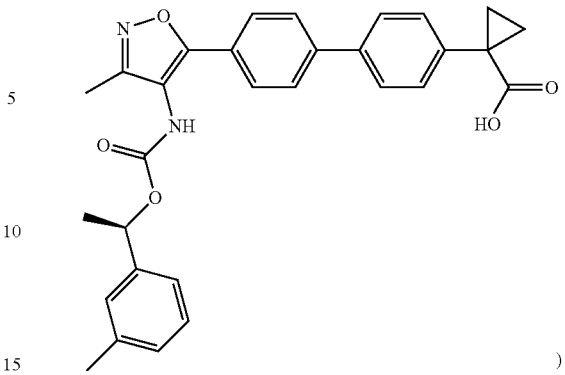

added in the saturation studies). The injected dose was 101±59 MBq (n=16) and the injected mass was 40±16 ng/kg (n=11; using tracer dose only).

Beginning at the start of each injection, a 120-minute time-of-flight list-mode acquisition on the mCT PET/CT scanner (Siemens Medical Solutions USA, Inc.) was performed. Dynamic PET scan data were reconstructed with corrections for point-spread function, attenuation, normalization, scatter, randoms, and dead time using a 3D OP-OSEM TOF algorithm. PET images were reconstructed into 33 frames, with the following frame timing: 6×30 sec; 3×1 min; 2×2 min; 22×5 min. Each frame contained 400×400×111 (x,y,z) voxels (2.04×2.04×2.0 mm).

5. Plasma PK Measurements a) Blocking Study

Blood samples for PK for each blockade study session were obtained at −1, 60, 90, 120, 150, 210, 240 and 270 minutes after the start of BMS-986020 bolus plus infusion. Red cells were precipitated at 3200 rpm for 10 minutes at 10° C.; the plasma was divided into two aliquots and frozen at −80° C. until shipped for analysis.

b) Saturation Study

Blood samples were also collected for the last three saturation studies at −5, 60, 90 and 120 minutes after the start of [$^{11}$C]-BMT-136088 bolus plus infusion with non-tracer doses (n=4). Red cells were precipitated at 3200 rpm for 10 minutes at 10° C.; the plasma was divided into two aliquots and frozen at −80° C. until shipped for analysis. The goal of these measurements was to compare the plasma concentrations estimated from measurements of [$^{11}$C]-BMT-136088 and its metabolism using gamma counters and HPLC systems, to that from measurement of unlabeled BMT-136088 using mass spectrometry.

6. Regions of Interest Delineation and Time-Activity Curve Computation a) Heart Regions of Interest Regions of interest (ROIs) were manually drawn on the heart using CT images collected before each PET scan. These ROIs included the myocardium and blood pools (ventricles and atria), which cannot be separated on these CT images. Additional ROIs were drawn for the right and left ventricles on early PET images (0-5 min after the beginning of the tracer injection) to evaluate the suitability of the ventricles to compute the input function for the lungs.

b) Lung Regions of Interest

The lungs were semi-automatically delineated using CT images collected before each PET scan.

First, the lungs were segmented based on the CT image values in Hounsfield scale (−1000<HU<−200), using a region growing algorithm and seeds manually placed at the center of the lungs;

The trachea, and occasionally the air in the stomach were manually excluded from the segmentation results;

The segmented lung ROIs were divided into right and left ROIs by manually selecting a plane separating the left and right side of the animal (animals were lying in supine position, but this plane was not always perfectly vertical);

The right and left ROIs were further divided into three smaller ROIs: lower lung, mid lung, and upper lung. The upper lung was defined as the part of the lung above the heart; the lower lung was defined as the part of the lung that is less than 5 slices (~1 cm) above the topmost axial slice where the top of the liver can be seen.

The lung time-activity curves (TACs) were computed for each ROI and expressed in kBq/cm$^3$. The lung ROI contains lung tissue, blood, and air. In particular, the lung density may change from scan to scan due to (slight) changes in animal positioning, which can change the left-right location of the heart and change which lung tends to be compressed by the heart. Therefore an estimate of the density of lung ROIs was estimated to convert the TAC units from kBq/cm$^3$ to kBq/g, as follows. The CT images were converted from Hounsfield scale to linear attenuation values (in cm$^{-1}$) for 511 KeV photons. These attenuation values were assumed to be linearly proportional to mass for soft tissue (e.g., lung and heart) and the heart density was assumed to be 1 g/cm$^3$.

7. Computation of Volumes of Distribution

The volumes of distribution (VT) were estimated using kinetic modeling and equilibrium analysis (EA).

In all methods, a correction was applied to take into account the radioactivity from the blood compartment.

a) Kinetic Modeling

For kinetic modeling, three compartmental models and the multilinear analysis MA1 were tested. For the first two compartmental models and for MA1, it was assumed that no radioactive metabolites enter lung tissue. The three compartmental models were:

the one-tissue compartment model
the two-tissue compartment model
another two-tissue compartment model, with one tissue compartment for [$^{11}$C]-BMT-136088 and one compartment for metabolites.

b) Equilibrium Analysis

For equilibrium analysis, the volumes of distribution were computed as the ratio of the average ROI activity to the average metabolite-corrected plasma concentration. Both averages were computed from 90 to 120 minutes after the start of the [$^{11}$C]-BMT-136088 bolus plus infusion.

Study Results

1. [$^{11}$C]-BMT-136088 Test-Retest Study Results

Test-retest variability was better (i.e., smaller variability) after density correction, and slightly better after correction for blood activity. With EA and both corrections, the test-retest variability was −1±11% and −2±10% in the right and left ROIs corresponding to the mid and upper lung. With MA1, results were not available for animal A1, since only venous sampling was available on that day. For animal A2, the test-retest variability was −8% and −5% in the right and left ROIs corresponding to the mid and upper lung. On the other hand, test-retest variability was worse in the lower lung ROIs, which were close to the liver. Factors such as attenuation correction bias due to respiratory motion or scatter may have contributed to larger variability there.

2. [$^{11}$C]-BMT-136088 Saturation Study Results a) [$^{11}$C]-BMT-136088 ED$_{50}$ Estimation All ED$_{50}$ estimates are consistently in the 36-56 µg/kg range, with estimates obtained with MA1 and density correction being more precise (lower SD or standard error) due to the more consistent VT estimates obtained with MA1 after density correction. With all corrections and MA1, [$^{11}$C]-BMT-136088 ED$_{50}$ was estimated to be 36±15 µg/kg, and the binding potential of [$^{11}$C]-BMT-136088 was estimated to be 1.1±0.1.

b) [$^{11}$C]-BMT-136088 Plasma Concentration in Saturation Study

The plasma concentration of [$^{11}$C]-BMT-136088 measured in plasma increased linearly with the injected mass of [$^{11}$C]-BMT-136088 (with a slope of 0.92 nM/(µg/kg)).

c) [$^{11}$C]-BMT-136088 IC$_{50}$ and In Vivo K$_D$ Estimation

Due to very linear relationship between plasma concentration and injected dose for [$^{11}$C]-BMT-136088, the VT versus plasma concentration relationships were very similar to the VT versus injected mass relationship. Using MA1 and all corrections, the IC$_{50}$ of [$^{11}$C]-BMT-136088 was estimated to be 28±12 nM. Using the average plasma free fraction measured during the saturation studies for [$^{11}$C]-BMT-136088 (0.2%), the in vivo K$_D$ of [$^{11}$C]-BMT-136088 was thus estimated to be 55 pM.

3. [$^{11}$C]-BMT-136088 Blocking Study with BMS-986020

Using V$_T$ values estimated with MA1 and all corrections, including lung density and blood radioactivity, the blockade effect of BMS-986020 was 54±11%.

Taking into account the results of the saturation study and the estimation of [$^{11}$C]-BMT-136088 binding potential BP$_{ND}$ (1.1±0.1), the maximum expected blockade effect would be 52%. Therefore, BMS-986020 occupancy of LPA1 binding was estimated to be 103±20% at 1.25 mg/kg, i.e., complete receptor blockade.

Study Conclusions

[$^{11}$C]-BMT-136088 volumes of distribution were more reliably estimated with kinetic analysis and the MA1 method, after correction for lung density (and less critically, blood volume).

[$^{11}$C]-BMT-136088 binding potential BPND was estimated to be 1.1±0.1, indicating that, at equilibrium, about 50% of the tracer in lung (excluding blood) was specifically bound to LPA1 sites. If this relationship holds true in humans, this tracer is highly suitable for performance of human occupancy studies.

[$^{11}$C]-BMT-136088 ED$_{50}$, plasma IC$_{50}$ and in vivo K$_D$ were evaluated to be 36±15 µg/kg, 28±12 nM, and 55 pM, respectively.

Based on the above ED$_{50}$, the tracer dose limit for [$^{11}$C]-BMT-136088 was estimated to be 1.9 µg/kg (in order to occupy less than 5% of LPAI sites).BMS-986020 at 1.25 mg/kg fully (that is, ~100% occupancy) blocked [$^{11}$C]-BMT-136088 binding sites in rhesus monkeys

What is claimed is:

1. A compound comprising a radiolabeled LPA1 receptor antagonist or a pharmaceutically acceptable salt thereof, wherein the LPA1 receptor antagonist is labeled with a position emitting radionuclide which is an isotope of carbon or fluorine for use in positron emission tomography wherein the compound has the structure:

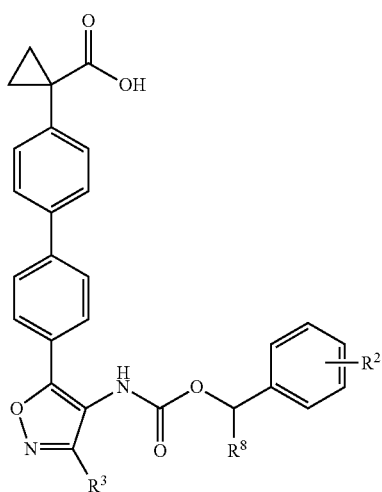
or a pharmaceutically acceptable salt thereof, wherein:
$R^8$ is H or $CH_3$;
$R^2$ is $^{18}F$, $^{11}CH_3$, $-CH_2{}^{18}F$, $^{11}C$, or
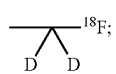
and
$R^3$ is $CH_3$.
2. The compound of claim 1 wherein the radiolabeled LPA1 receptor antagonist or a pharmaceutically acceptable salt thereof has the following structure:
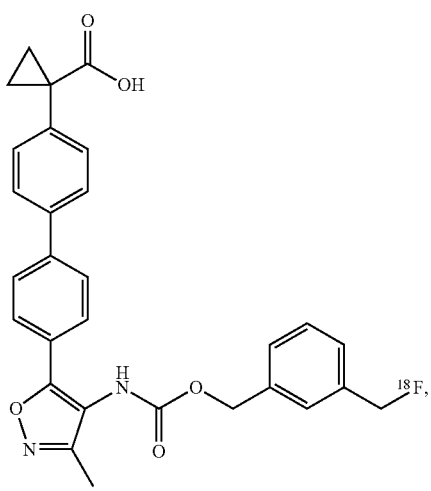
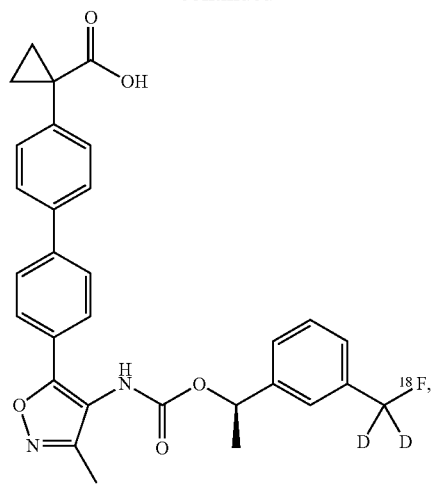
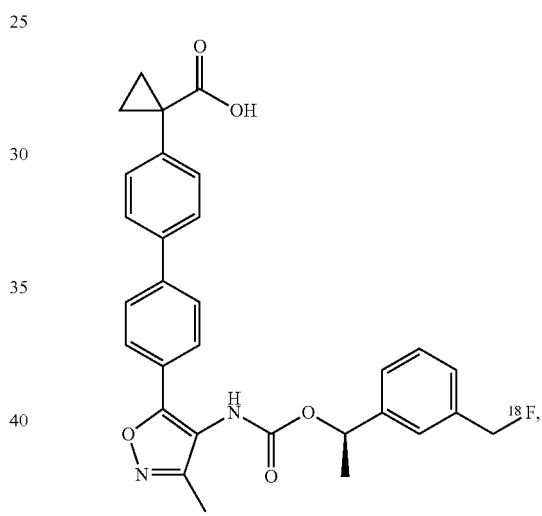
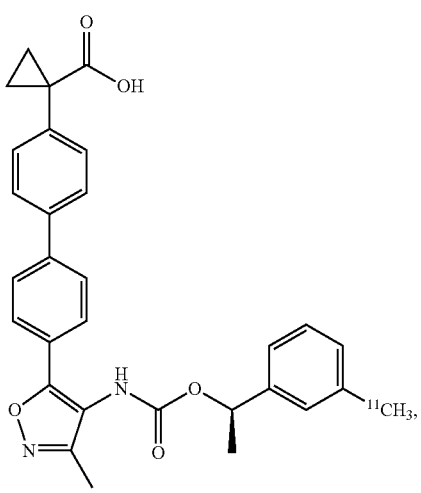

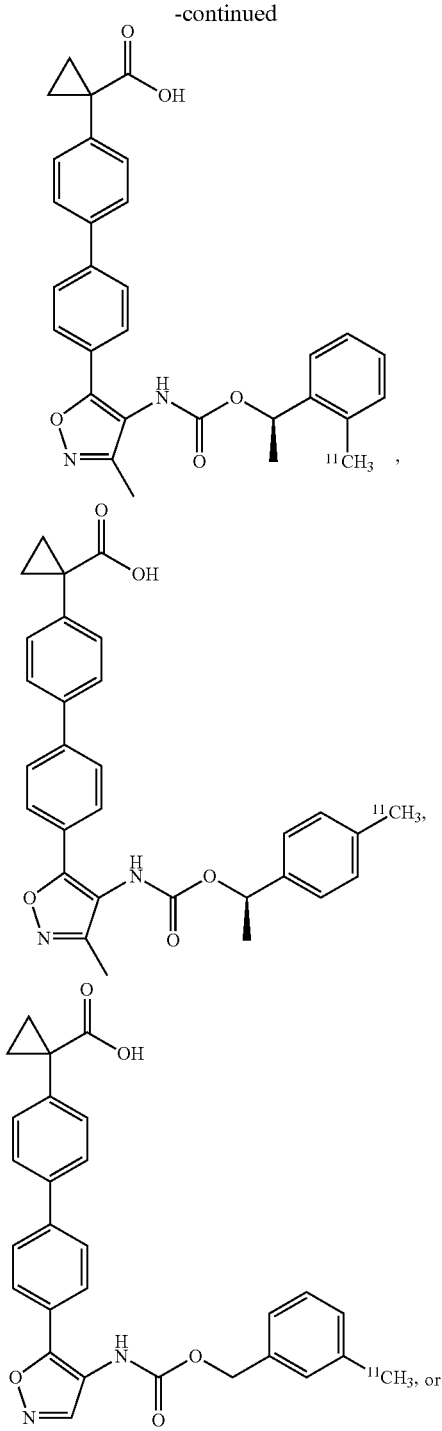
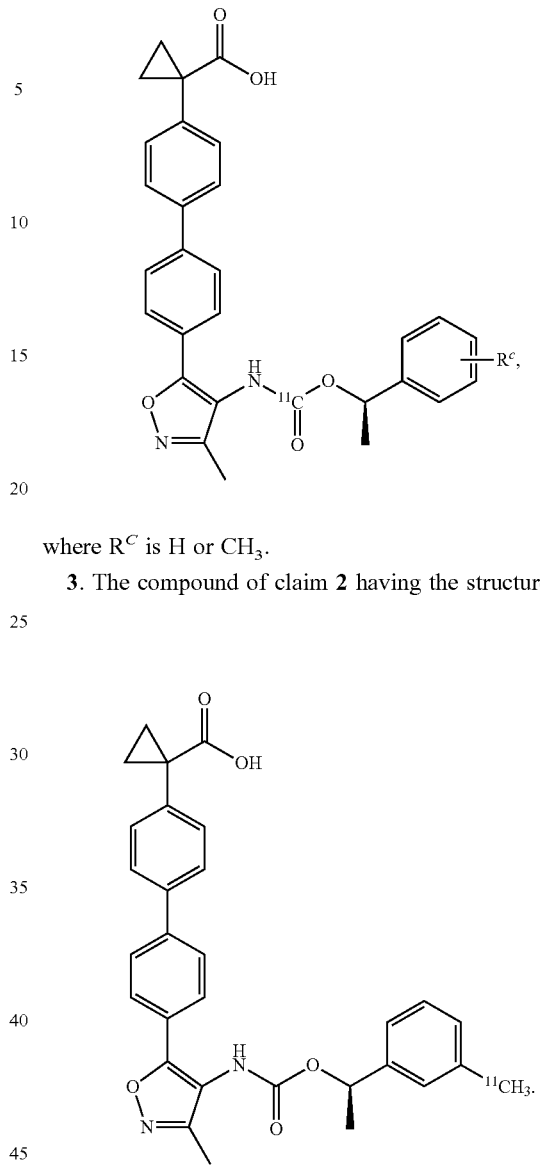
where $R^c$ is H or $CH_3$.
3. The compound of claim 2 having the structure
4. A diagnostic or radiopharmaceutical composition for imaging LPA1 receptors comprising a compound as defined in claim 1 or a pharmaceutically acceptable salt thereof and a pharmaceutically acceptable carrier therefor.
* * * * *